(12) United States Patent
Hancock et al.

(10) Patent No.: US 10,820,937 B2
(45) Date of Patent: Nov. 3, 2020

(54) ELECTROSURGICAL INSTRUMENT HAVING MULTIPLE TREATMENT MODALITIES

(71) Applicant: CREO MEDICAL LIMITED, Beaufort Park Way (GB)

(72) Inventors: Christopher Paul Hancock, Bath and North East Somerset (GB); Shaun Preston, Monmouthshire (GB); Francis Amoah, Monmouthshire (GB); Malcolm White, Monmouthshire (GB); Zacharias Tsiamoulos, Canterbury (GB); Brian Saunders, Rickmansworth (GB)

(73) Assignee: CREO MEDICAL LIMITED, Chepstow (GB)

( * ) Notice: Subject to any disclaimer, the term of this patent is extended or adjusted under 35 U.S.C. 154(b) by 330 days.

(21) Appl. No.: 15/781,442

(22) PCT Filed: Mar. 2, 2017

(86) PCT No.: PCT/EP2017/054899
§ 371 (c)(1),
(2) Date: Jun. 4, 2018

(87) PCT Pub. No.: WO2017/149072
PCT Pub. Date: Sep. 8, 2017

(65) Prior Publication Data
US 2019/0083159 A1     Mar. 21, 2019

(30) Foreign Application Priority Data

Mar. 4, 2016   (GB) .................................. 1603744.2

(51) Int. Cl.
*A61B 18/18*  (2006.01)
*A61B 18/04*  (2006.01)
(Continued)

(52) U.S. Cl.
CPC ........ *A61B 18/042* (2013.01); *A61B 18/1477* (2013.01); *A61B 18/1482* (2013.01);
(Continued)

(58) Field of Classification Search
CPC .............. A61B 18/042; A61B 18/1477; A61B 18/1482; A61B 18/1815;
(Continued)

(56) References Cited

U.S. PATENT DOCUMENTS

| 10,342,595 | B2 * | 7/2019 | Hancock ............ A61B 18/1815 |
| 2004/0143252 | A1 | 7/2004 | Hurst |

(Continued)

FOREIGN PATENT DOCUMENTS

| GB | 2503673 A | 1/2010 |
| GB | 2487199 A | 7/2014 |

(Continued)

OTHER PUBLICATIONS

British Search Report issued in British Patent Application No. GB1603744.2 dated Aug. 8, 2016.
(Continued)

*Primary Examiner* — Michael F Peffley
(74) *Attorney, Agent, or Firm* — Arent Fox LLP

(57) ABSTRACT

An electrosurgical instrument which is capable of selective operation in any of (i) a plasma-generating mode for surface coagulation, (ii) a non-ionising radiation mode for deeper coagulation, e.g. using microwave energy, and (iii) a liquid administration mode for conveying liquid to a treatment site, e.g. to constrict a bleeding vessel so that a clinician can get control of the bleed. These operating modes may be provided in an electrosurgical instrument that is physically configured to be suitable for applying pressure to a tissue vessel, e.g. to act as a tamponade to stem bleeding.

34 Claims, 18 Drawing Sheets

(51) Int. Cl.
*A61B 18/14* (2006.01)
*A61B 18/00* (2006.01)

(52) U.S. Cl.
CPC .............. *A61B 18/1815* (2013.01); *A61B 2018/00029* (2013.01); *A61B 2018/00077* (2013.01); *A61B 2018/00113* (2013.01); *A61B 2018/00166* (2013.01); *A61B 2018/00583* (2013.01); *A61B 2018/00589* (2013.01); *A61B 2018/00708* (2013.01); *A61B 2018/00875* (2013.01); *A61B 2018/00994* (2013.01); *A61B 2018/1435* (2013.01); *A61B 2018/1846* (2013.01); *A61B 2018/1861* (2013.01); *A61B 2018/1869* (2013.01); *A61B 2018/1892* (2013.01)

(58) Field of Classification Search
CPC ........... A61B 2018/00029; A61B 2018/00077; A61B 2018/00113; A61B 2018/00166; A61B 2018/00583; A61B 2018/00589; A61B 2018/00708; A61B 2018/00875; A61B 2018/00994; A61B 2018/1435; A61B 2018/1846; A61B 2018/1861; A61B 2018/1869; A61B 2018/1892
See application file for complete search history.

(56) References Cited

U.S. PATENT DOCUMENTS

| | | | |
|---|---|---|---|
| 2012/0172789 | A1 | 7/2012 | Fischer et al. |
| 2012/0259326 | A1* | 10/2012 | Brannan .......... A61B 17/00234 606/33 |
| 2013/0218069 | A1 | 8/2013 | Neugebauer et al. |
| 2014/0358140 | A1 | 12/2014 | Emmons et al. |
| 2015/0196353 | A1* | 7/2015 | Hancock ............ A61B 18/1815 606/46 |
| 2017/0189114 | A1* | 7/2017 | Hancock ............ A61B 18/1815 |
| 2019/0090339 | A1* | 3/2019 | Frame .................. A61L 2/0011 |

FOREIGN PATENT DOCUMENTS

| | | |
|---|---|---|
| GB | 2520197 A | 5/2015 |
| GB | 2521611 A | 7/2015 |
| WO | WO 2014/184544 A1 | 11/2014 |

OTHER PUBLICATIONS

International Preliminary Report on Patentabilits issued in PCT Application No. PCT/EP2017/054899 dated Feb. 16, 2013.
International Search Report and Written Opinion issued in PCT Application No. PCT/EP2017/054899 dated Aug. 31, 2017.

* cited by examiner

ELECTROSURGICAL INSTRUMENT HAVING MULTIPLE TREATMENT MODALITIES

CROSS-REFERENCE TO RELATED APPLICATIONS

This application is a National Stage entry of International Application No. PCT/EP2017/054899, filed Mar. 2, 2017, which claims priority to British Patent Application No. 1603744.2, Mar. 4, 2016. The disclosures of the priority applications are incorporated in their entirety herein by reference.

FIELD OF THE INVENTION

The invention relates to an electrosurgical instrument for stemming bleeding in surgical procedures. In particular, the invention relates to an electrosurgical instrument that is capable of operating in a plurality of different modes, so that an operating clinician may be able to choose a mode in response to a given scenario without necessitating an instrument change.

BACKGROUND TO THE INVENTION

Argon plasma coagulation (APC) is a known surgical technique for controlling surface bleeding in a manner that does not require physical contact between a surgical probe delivering the plasma and the lesion. APC can be used in any type of surgical procedure, e.g. in open surgery or in laparoscopic procedures. APC can also be performed endoscopically whereby a jet of argon gas is directed through a probe passed through an endoscope. Ionization of the argon gas as it is emitted creates the plasma that causes coagulation.

It is also known that microwave energy can be used to perform coagulation in deeper-lying tissues.

It is also known to administer liquid medication such as adrenaline to the site of a bleed, in order to constrict blood vessels during severe bleeds.

SUMMARY OF THE INVENTION

At its most general the present invention provides an electrosurgical instrument which is capable of selective operation in any of (i) a plasma-generating mode for surface coagulation, (ii) a non-ionising radiation mode for deeper coagulation, e.g. using microwave energy, and (iii) a liquid administration mode for conveying liquid to a treatment site, e.g. to constrict a bleeding vessel so that a clinician can get control of the bleed. These operating modes may be provided in an electrosurgical instrument that is physically configured to be suitable for applying pressure to a tissue vessel, e.g. to act as a tamponade to stem bleeding.

The electrosurgical instrument of the invention may be suitable for use in any type of procedure, e.g. open surgery (such as liver resection), laparoscopic surgery, etc. For example, the instrument may be dimensioned to fit within an instrument channel of a surgical scoping device, e.g. an endoscope, laparoscope or the like.

This is broadly achieved by having a first electrode and a second electrode which can sustain a plasma-generating electric field between them, in the presence of a flow of gas, and a liquid channel in fluid communication with a probe tip. More specifically, in order to provide the three operating modes discussed above, a first aspect of the present invention provides an electrosurgical instrument having an elongate probe comprising: a coaxial transmission line for conveying radiofrequency (RF) and/or microwave electromagnetic (EM) radiation; a probe tip at a distal end of the coaxial transmission line for receiving the RF and/or microwave energy; a liquid channel for conveying liquid to the probe tip; and a gas channel for conveying gas to the probe tip; wherein the coaxial transmission line includes an inner conductor, an outer conductor, and a first dielectric material separating the inner conductor from the outer conductor, wherein the probe tip comprises a second dielectric material having a probe tip channel running therethrough, the probe tip channel being in fluid communication with the liquid channel and terminating in an aperture at its distal end; wherein the probe tip includes a first electrode connected to the inner conductor of the coaxial transmission line and a second electrode connected to the outer conductor of the coaxial transmission line, the first electrode and the second electrode being selectively operable in a plasma generating mode or a non-ionising radiation mode, wherein, in the plasma generating mode, the first electrode and second electrode are arranged around a flow path of gas from the gas channel, whereby the RF and/or microwave EM energy from the coaxial transmission line is deliverable to strike and sustain a thermal or non-thermal plasma in gas delivered along the flow path, and wherein, in the non-ionising radiation mode, at least one of the first electrode and the second electrode is configured as a radiating antenna structure for emitting a microwave EM field outwardly from the probe tip.

In use, the instrument can be used in any of the three operation modes discussed above. In the plasma generating mode, gas is delivered through the gas channel and RF and/or microwave energy is used to strike and sustain a plasma in the gas. The RF energy may be delivered as an initial pulse to strike the plasma, while the microwave energy may be delivered after the initial pulse to sustain the plasma. In the non-ionising radiation mode, microwave energy may be deliver to the probe tip in the absence of gas. In this mode, the radiating antenna structure emits a microwave EM field. In the liquid administration mode, a liquid is delivered along the liquid channel and through the aperture to a treatment site. This is preferably done in the absence of gas and RF/microwave energy.

The instrument may be selectively operable in a RF delivery mode, in which RF energy is coupled out of the device between the first electrode and second electrode. The RF energy may be delivered separately or simultaneously with the microwave EM energy, e.g. when the device is in the non-ionising radiation mode.

The first electrode and second electrode may be movable relative to each other to adopt different configurations for the plasma generating mode and non-ionising radiation mode respectively. For example, the first electrode may be movable along a longitudinal axis of the elongate probe to project beyond a distal end of the second electrode when operating in the non-ionising mode. The relative movement of the electrodes may occur automatically upon selection of a given operating mode by the user.

The gas channel and liquid channel are preferably separate pathways, i.e. they are not in fluid communication with each other before reaching a distal end of the instrument. Either one or both of the liquid channel and the gas channel may be located inside the coaxial transmission line, i.e. as a passageway lying within the outer diameter of the outer conductor. For example, the liquid channel and/or gas channel may be formed by a longitudinal passageway through the first dielectric. In another example, the inner conductor may be hollow, i.e. have one or more longitudinal passageways running therethrough. Thus, the liquid channel and/or the gas channel may be located inside the inner conductor of the coaxial transmission line. This arrangement may enable a more compact device.

In this specification "microwave" may be used broadly to indicate a frequency range of 400 MHz to 100 GHz, but preferably the range 1 GHz to 60 GHz. Specific frequencies that have been considered are: 915 MHz, 2.45 GHz, 3.3 GHz, 5.8 GHz, 10 GHz, 14.5 GHz and 24 GHz. In contrast, this specification uses "radiofrequency" or "RF" to indicate a frequency range that is at least three orders of magnitude lower, e.g. up to 300 MHz, preferably 10 kHz to 1 MHz.

In order to convey the RF energy without breakdown, the dielectric material separating the inner and outer conductors of the coaxial transmission line may have a higher dielectric strength (i.e. a higher breakdown electric field) than is necessary if microwave energy alone is conveyed along the coaxial transmission line. This may be done by using a single layer of dielectric material with dielectric strength suitable for use with both RF and microwave energy, for example polyimide (e.g. Kapton®) or a suitable ceramic having a dielectric constant greater than 3.0 at 1 MHz. In another embodiment, the first dielectric material may comprise a multi-layered dielectric structure including a first layer formed from a dielectric material having a first dielectric strength and a second layer formed from a dielectric material having a second dielectric strength, the second dielectric strength being lower than the first dielectric strength. The dielectric material of the second layer may be selected to exhibit low loss for microwave energy, i.e. have a dielectric constant less than 2.1 and loss tangent less than 0.0003 (preferably equal to or less than 0.0001) at the frequency of the microwave EM energy. The first layer may be thinner than the second layer. The first layer may function to protect against breakdown when conveying the RF energy. The thickness of the first layer is preferably selected to ensure a negligible increase in dielectric loss. The multi-layered structure may comprise a third layer formed from a dielectric material having a third dielectric strength, which is higher than the second dielectric strength and may be the same as the first dielectric strength. The third layer may be located on the opposite side of the second layer from the first layer. In one example, the multi-layered structure may comprise a pair of Kapton® layers sandwiching a layer of expanded PTFE. In another example, the multi-layered structure may comprise a pair of fluorinated ethylene propylene (FEP) sandwiching a layer of polyethylene foam (e.g. Eccostock® PP).

The coaxial transmission line may have an outside diameter of no more than 10 mm, and more preferably no more than 5 mm. Most preferably, the coaxial transmission line may have an outside diameter no more than 2.5 mm so that the elongate probe can be placed inside the channel of an endoscope. The dielectric material separating the inner conductor from the outer conductor may be no more than 1 mm thick, and more preferably no more than 0.5 mm thick. The dielectric constant of the dielectric material may be no more than 5, and more preferably no more than 3, and most preferably no more than 2.5. The dielectric material may be polytetrafluoroethylene (PTFE). At least one of the inner or outer conductors may be made from silver. The thickness of the inner and outer conductors may be no more than 50 microns, and preferably no more than 25 microns, and most preferably no more than 10 microns. These thicknesses are sufficient for transmission of the RF and microwave EM energy along the coaxial transmission line but are sufficiently small to enable the inner conductor to have one or more passageways formed therethrough.

The probe tip may be physically configured to be suitable to apply pressure to a bleed site during treatment. For example, the probe tip may have a proximal end connected to the distal end of the coaxial transmission line, and a distal end opposite to the proximal end that is shaped in a smoothly contoured manner to be suitable for applying a pressure spot to a target area. The probe tip channel joins the proximal end and the distal end. The aperture is located at the distal end of the probe tip channel.

The probe tip may be connected to the coaxial transmission line in any suitable manner, e.g. crimping, soldering, adhesive, etc.

The radiating antenna structure may be a monopolar structure formed by the first electrode, or may be a dipole antenna formed by both the first electrode and second electrode. The radiating antenna structure may comprise an electrically conductive structure formed by either the first electrode, the second electrode, or a combination of both the first electrode and the second electrode. The conducting structure may be located on the surface of the probe tip, and may also be at least partially embedded in the material.

In order to be able to emit a cylindrically isotropic microwave field, the conducting structure and/or the entire probe tip may have cylindrical symmetry (herein, "axis of symmetry" refers to the axis of cylindrical symmetry unless stated otherwise). This ensures that the orientation of the microwave field is independent of rotation of the probe tip around the axis of symmetry, during use of the probe. The longitudinal axis of the probe tip channel (i.e. an axis aligned with the axis of the coaxial transmission line) is preferably parallel to the axis of symmetry of the probe tip itself. More preferably, the axis of symmetry of the probe tip is the same as the longitudinal axis of the probe tip channel so that the probe tip channel is located at the centre of the probe tip, when viewed along the axis of symmetry of the probe tip. The probe tip may be domed, conical, frustoconical or ball-shaped. Alternatively the probe tip may include a cylindrical section integrally formed with a hemispherical distal end section. When the probe tip is connected to the coaxial transmission line, the coaxial transmission line (at least in the region near the distal end) and the probe tip channel may have substantially the same long axis.

The second dielectric material is preferably a low loss, mechanically strong material. Here, "low loss" refers to a material through which microwaves may pass without a substantial loss of energy into the material. The second dielectric material is preferably sufficiently rigid that mechanical pressure may be applied to the site of a bleed using the instrument without substantial deformation of the probe tip occurring. The second dielectric material may be PEEK or a suitable ceramic, e.g. Macor®. The second dielectric material may be continuous with the first dielectric material.

To operate in the plasma generating mode, a high electric field for striking a plasma may be generated by creating a high impedance condition for either the RF energy or the microwave EM energy at the probe tip. This can be achieved through the selection of a suitable geometry for the first and second electrodes. For example, a piece of insulating dielectric material, such as quartz or other similarly low loss material, may be located between the first and second electrodes. The insulating dielectric material may be the same as the second dielectric material that makes up the probe tip, and may also be continuous therewith.

In the plasma generating mode, the RF energy received by the probe tip may be for striking the plasma, and may be received as a high voltage pulse. The high voltage pulse may be predetermined period of CW RF energy, i.e. may comprise a series (i.e. a plurality) of RF cycles, e.g. a 1 ms burst of sine waves with a frequency of 100 kHz. The microwave energy can be used to sustain the plasma, i.e. delivering power into the plasma to maintain the state of ionisation. This may also be received as a pulse. The plasma may be struck repeatedly in a manner to produce a quasi-continuous beam of plasma. The advantage of this arrangement over devices which use only RF energy is that the plasma will not collapse due to capacitive loading or changing from a dry to wet environment. From the plasma generating (and sustaining) mode, the electrosurgical instrument is also able to switch to a microwave emission mode suitable for deeper coagulation, where the conducting structure formed by the first and/or second electrode is able to act as a radiating microwave antenna structure as discussed above.

It is desirable that heating (preferably, internal heating) and therefore coagulation occurs both at the distal end of the probe tip and also around the sides of the probe tip. Heating should be strongest at the distal end of the probe tip, since if the strongest heating were at the proximal end, tapering off of the heating towards the distal end might result in non-uniform heating along the length of the probe tip. In order to obtain the strongest heating at the distal end of the probe tip, microwave/RF energy is preferably fed to part of the conducting structure (formed by one or both of the first and second electrodes) which is located at or near to the distal end of the probe tip, via a transmission line structure. Connection at the proximal end is possible, but not preferred since, in use, there may be some attenuation of the power between the proximal end and the distal end because of absorption of the microwave/RF energy by biological tissue touching the structure.

In one embodiment, the probe tip may include a helical electrically conductive structure. The helical electrically conductive structure may include a first outer helical electrode and an inner helical electrode having the same pitch as the first outer helical electrode, connected to the coaxial transmission line at a feed point located at or near the proximal end of the probe tip. The first outer helical electrode is disposed on the outer surface of the probe tip and the inner helical electrode is disposed radially inward from the first outer helical electrode, and may be embedded in the dielectric material of the probe tip, at least partially below the outer surface.

A waveguide or transmission line structure is formed between the inner helical electrode and the first outer helical electrode. Accordingly, the first outer helical electrode and the inner helical electrode may be formed of strips of conducting material wherein the inner helical electrode has a smaller diameter than the first outer helical electrode and follows a substantially parallel path thereto, to ensure significant overlap between the facing (inner) surfaces of the first outer helical electrode and the inner helical electrode, to convey RF or microwave EM energy therebetween. Together, the inner helical electrode and first outer helical electrode may form a helical microstrip transmission line, which is arranged to convey the energy from a feed point at the proximal end of the probe tip to the distal end of the probe tip.

In an alternative configuration, the helical electrically conductive structure comprises a first helical electrode and a second helical electrode formed in an axially offset relationship on the outer surface of the probe tip. The first helical electrode and second helical electrode are electrically isolated from each other to form a coplanar transmission line.

The impedance of the helical electrically conductive structure formed by the two helical electrodes in the microstrip or coplanar arrangements discussed above may be matched to the coaxial transmission line. This may be done using a matching transformer or by selecting the geometry of the structure so that its characteristic impedance is approximately 50Ω.

In addition to the microstrip transmission line for feeding the EM energy to the distal end of the probe tip, a second outer helical electrode, diametrically opposite to the first outer helical electrode may be disposed on the outer surface of the probe tip. In appearance, the diametrically opposed second outer helical electrode runs parallel to the first outer helical electrode at a fixed axial offset, so that the coils of the first and second outers alternate with each other. The second outer helical electrode may be identical to, or substantially identical to the first outer helical electrode. At its distal end, the second outer helical electrode may be connected to the inner helical electrode, so that when microwave or RF energy is transmitted to the distal end of the probe tip by the helical microstrip transmission line, corresponding microwave or RF signals can be excited between the first and second outer helical electrodes, which will then travel back towards the proximal end of the probe tip, along the helical spaces between the first and second outer helical electrodes. The connection between the distal ends of the inner helical electrode and the second outer helical electrode does not cover the aperture on the probe tip, so that it is not occluded. In this case, the inner helical electrode is connected to the inner conductor and the first outer helical electrode is connected to the outer conductor at a feed point located at the distal end of the probe tip. The proximal end of the second outer helical electrode is open to avoid short circuiting the electrodes.

In order to be able to perform processes such as argon plasma coagulation (APC), and the like, it is necessary for an output of the gas channel to be located in a position whereby gas exiting the gas channel passes over a region between the first electrode and the second electrode where the high energy electric field may form. Thus, when a high energy electric field is generated between the first electrode and the second electrode, gas which passes through said electric field will be ionized to generate a plasma. The separation of the first and second electrodes determines the magnitude of the electric field. In the helical structure discussed above, the separation of the helical electrodes may be varied along the helix in order to control where plasma generation occurs, i.e. by creating preferential ionisation sites.

A gas channel with an annular cross section may be defined by an outer jacket located outside the outer surface of the coaxial transmission line. In this case, the gas channel is defined by the space between the inner surface of the jacket and the outer surface of the coaxial transmission line. Spacers may be employed to ensure that there is sufficient spacing between the jacket and the coaxial transmission line to ensure that a sufficient amount of gas may pass through unimpeded. Alternatively, the inner surface of the jacket may be in contact with the outer surface of the coaxial transmission line, and gas channels may be formed as bores through along the wall of the jacket itself.

An input port may be located at the proximal end of the gas channel, for connecting to a gas source such as a pressurized gas canister. The gas source may be a source of argon, or any other suitable gas, e.g. carbon dioxide, helium, nitrogen, a mixture of air and any one of these gases, i.e. 10% air/90% helium. At the distal end of the gas channel, gas fed into the input port at the proximal end of the channel is fed out over the surface of the first and second outer helical electrodes, such that a plasma can be struck by the high electric field between the electrodes.

In another embodiment (herein referred to as a "ring configuration"), the first electrode may be in the form of a conducting shell on the inner surface of the probe tip channel, which may be formed as a longitudinal extension of the inner conductor. The second electrode may be in the form of a conducting ring on the outer surface of the second dielectric material of the probe tip. The conducting ring is electrically connected to the outer conductor, preferably by a strip of conducting material located on the outer surface of the second dielectric material. The first and second electrodes are preferably electrically isolated from each other in order to avoid a short circuit therebetween.

In the ring configuration, in order for the high electric field generated between the first electrode and the second electrode to strike a plasma, the gas channel must have its distal end at or near the region between the first electrode and the second electrode, for example by using the outer jacket arrangement as described above, or otherwise. In order to administer a liquid to a target area of biological tissue, the liquid channel must also be in fluid communication with the probe tip channel.

Accordingly, in an alternative embodiment in order to separate the gas channel from the liquid channel, a multi-lumen structure may be located inside the hollow channel formed by the inner conductor of the coaxial transmission line. In one embodiment of the multi-lumen structure, a central liquid channel may be defined, which is surrounded by one or more peripheral gas channels, separated from the liquid channel by one or more partition walls. A distal end of the multi-lumen structure has a liquid exit aperture and at least one gas exit aperture, terminating the liquid channel and at least one gas channel respectively. The outer diameter of the multi-lumen structure is no more than the diameter of the hollow channel defined by the inner conductor of the coaxial transmission line. In another embodiment, a protective coating may be located on the inner surface of the inner conductor of the coaxial transmission line. In this case, the multi-lumen structure is located inside the hollow channel formed by the inner surface of the inner coating. The multi-lumen structure may be removable from the channel in which it is located, such that different structures may be used for different procedures, depending on the requirements of that procedure. A distal end surface of the multi-lumen structure may be located at the distal end of the coaxial transmission line. In this case, in order for the gas to exit the gas channel to a region which is located between the first electrode and the second electrode, a gas exit channel may be provided between the gas channel and terminating in a gas exit aperture on the outer surface of the outer conductor, or on the outer surface of the probe tip. The gas exit channel is preferably obliquely oriented with respect to the gas channel. The gas exit channel may pass through one or more of the inner conductor, the outer conductor, the first dielectric material and the second dielectric material. There may be a plurality of gas exit channels.

Depending on the way that gas is delivered to the instrument, the gas may need to be guided into a suitable stream in order for it to be effective. This can be achieved by shaping the peripheral gas channels of the gas exit aperture(s) to direct the gas to a desired location, e.g. to a region where the two electrodes are in close proximity (i.e. to a preferential ionisation region discussed above). The flow rate of the gas can also be altered by adjusting the cross sectional areas of the gas channels (the cross sectional area of each gas channel preferably being constant along most of its length), and the cross sectional area of the gas exit apertures, and in particular the size of the cross sectional area of the gas exit apertures relative to the cross sectional area of the gas channel(s). For example, to increase the flow rate at the gas exit aperture, the cross sectional area of the gas exit aperture may be smaller than the cross sectional area of the gas channel which it terminates.

In another embodiment, the first electrode and the second electrode may be in the form of a first conducting strip and a second conducting strip on the outer surface of the probe tip. The first and second conducting strips are preferably located on opposite sides of the aperture. The strips may be arranged so that when viewed down the long axis of the probe tip channel, the two strips appear substantially straight, and/or substantially parallel. The first conducting strip is connected to the inner conductor and the second conducting strip is connected to the outer conductor. The first conducting strip and the second conducting strip are preferably electrically isolated from each other in order to avoid a short-circuit occurring therebetween. In this arrangement, the gas channel may either be provided as part of a multi-lumen structure as described above, or as a result of an outer jacket spaced from the outer conductor. The distance between the conducting strips may decrease as they approach the distal end of the device, in order to create a preferential ionisation at the distal tip.

In another embodiment, the first electrode may be in the form of a first conducting strip on the outer surface of the second dielectric material, the first conducting strip comprising a first limb and a second limb, which are disposed on opposite sides of the outer surface of the second dielectric material, meeting at the distal end of the probe tip. The first conducting strip may be formed by wrapping a strip of conductive material around the probe tip. The first conducting strip is preferably connected to the inner conductor of the coaxial transmission line at the distal end of the probe tip. Accordingly, in this embodiment, it is preferable that the inner conductor of the coaxial transmission line, and more preferably, the whole of the coaxial transmission line, extends all the way to the distal end of the probe tip. A conductive connecting structure may be located at the distal end of the probe tip in order to connect the inner conductor with the first conducting strip. In this embodiment the second electrode may be in the form of a second conducting strip, located on an outer surface of the second dielectric material. The second conducting strip is preferably located at a position which is approximately halfway between the first limb and the second limb of the first conducting strip, on the outer surface of the probe tip. More preferably, the second conducting strip is removed 90 degrees from each of the first limb and the second limb of the first conducting strip. The second electrode may also include a third conducting strip, disposed on the outer surface of the probe tip at a position opposite to the second conducting strip. Preferably, the third conducting strip is located at a position which is approximately halfway between the first limb and the second limb of the first conducting strip, opposite to the second conducting strip. As with the second conducting strip, the third conducting strip is preferably removed by 90 degrees from each of the first limb and the second limb of the first conducting strip. The second and third conducting strips are preferably connected to the outer conductor of the coaxial transmission line at their proximal ends. Preferably, the outer conductor of the coaxial transmission line has first and second conductive projections which are located diametrically opposite to each other at a position at or near the proximal end of the probe tip. The proximal ends of each of the second and third conducting strips are then connected to the outer ends of the first and second conductive projections in order to electrically connect them to the outer conductor of the coaxial transmission line. In an embodiment as described above, the outer surface of the probe tip is divided into four approximately equal regions, each bounded by two of the of the first, second and third conducting strips. Then, in use, an electric field may be generated between each adjacent pair of conducting strips, allowing a plasma to form all the way around the outer surface of the probe tip, in a plasma-generating mode. In an alternative embodiment, the liquid channel and the gas channel may be the same channel.

The liquid may be delivered from the probe tip by a hollow needle, for example a hypodermic needle, having a first end and a second end, the needle passing through the aperture at the distal end of the probe tip channel. The first end of the needle may be in fluid communication with the liquid channel, so liquid in the liquid channel can enter the needle and the second end of the needle may be arranged to deliver liquid to a target area located outside the probe tip channel. Use of a needle allows a controlled, steady flow of liquid to be applied to a target area. The needle may extend for the whole length of the liquid channel.

Additionally, the needle may be adjustable between a retracted position and an exposed position, wherein when the needle is in an exposed position, the second end of the needle is located external to the probe tip, i.e. in contact with, or closely adjacent to the target area, and when the needle is in the retracted position, the second end of the needle remains inside the probe tip. Alternatively, when the needle is in a retracted position, the second end of the needle may be retracted all the way back inside the coaxial transmission line, or liquid channel to which the probe tip is connected. In order to effect the adjustment of the needle between the exposed and retracted positions, the electrosurgical instrument may be provided with needle-adjustment means, for example a guide wire may be attached at or near the first end of the needle, the guide wire passing along the liquid channel, so that adjustment of the needle can be controlled from the proximal end of the liquid channel. This enables adjustment of the needle while the device is in use. A needle feed tube may also be attached to the first end of the needle to supply the needle with a liquid to be administered to a target area. In this way, delivery of a liquid can be controlled more carefully, and there is no need to flood the entire channel with liquid in order to administer it, which can result in more economical use of the liquid.

At least part of the needle may be located within the probe tip channel, and may be affixed to a wall of the probe tip channel, for increased stability. The needle may be located in a needle guiding structure on a wall of the probe tip channel in order to ensure that during adjustment between the exposed and retracted positions, the long axis of the needle does not change its orientation relative to the long axis of the probe tip channel. This allows greater control during adjustment of the needle, and may, for example, ensure that the needle is not scraped laterally across biological tissue during adjustment while the instrument is in use. When an inner surface of the probe tip channel includes a conducting material, the needle is preferably insulated from said conducting material, for example by a layer of insulating material (e.g. Kapton® or PFTE) which may cover the whole inner surface of the conducting shell, or alternatively, cover only the part where the needle contacts said inner surface. In the case where the first and second electrodes are in the coaxial plasma-generating arrangement, rather than the inner surface of the probe tip channel, the inner surface of the second electrode is the relevant surface for the purposes of this paragraph.

The largest diameter of the needle may be smaller than the smallest diameter of the aperture or of the probe tip channel. In this case, a plug may be provided to form a fluid tight seal between the needle and the wall of the probe tip channel. Such a seal may allow injection of liquid to a target area from the needle when the liquid is in an exposed position, but prevent backflow of blood and other bodily fluids into the probe tip when the needle is in a retracted position, i.e. the seal may comprise a one-way valve. The plug may be formed from a non-rigid or resiliently deformable material which plugs the aperture, so that when the needle is in an exposed position, the plug exerts inward pressure on the outer surface of the needle, to form a fluid tight seal, and when the needle is in a retracted position, the resiliently deformable nature of the plug ensures that there is no hole present through the plug, i.e. seals shut the hole through which the needle can pass. The outermost end of the plug may lie flush with the surface of the probe tip, and may be shaped to form a continuous surface. Alternatively the plug may be located inside the probe tip channel, its outermost end spaced from the aperture. The plug may be any suitably durable material, e.g. silicone, PEEK or PTFE.

In selecting the dimensions of the instrument, a balance is struck between the thicknesses of the layers making up the coaxial transmission line and the diameter of the hollow defined by the inner surface of the inner conductor which aims to minimise the energy losses in the system whilst providing a suitable flow rates for gas and liquid delivery.

The coaxial transmission line may have an outside diameter of no more than 10 mm, and more preferably no more than 5 mm. Most preferably, the coaxial transmission line may have an outside diameter no more than 2.5 mm. Thus, the elongate probe may be sized to fit inside the instrument channel of a surgical scoping device, such as an endoscope, laparoscope or the like. The first dielectric material separating the inner conductor from the outer conductor may be no more than 1 mm thick, and more preferably no more than 0.5 mm thick. The dielectric constant of the first dielectric material may be no more than 5, and more preferably no more than 3, and most preferably no more than 2.5. The first dielectric material may be an expanded or low density polytetrafluoroethylene (PTFE), i.e. a material having a PTFE matrix containing air pockets, such as Plastolon®. Other materials may also be used, such as nylon or polyurethane.

The properties, e.g. thickness and dielectric constant of the first dielectric material may be selected so that it can withstand an RF peak voltage of at least 400 V, and preferably 800 V. This level of breakdown protection can be provided by the first dielectric material alone. However, in some examples, an additional layer of higher dielectric strength material (e.g. Kapton®) may be provided.

The probe tip may have a maximum diameter that is equal to or less than the outer diameter of the coaxial transmission line. In order to enable the instrument to be maneuvered easily, especially in examples where it is inserted through the instrument channel of a surgical scoping device, the axial length of the probe tip is preferably equal to or less than 10 mm.

The electrically conductive structure that forms the radiating antenna structure may be flexible, i.e. capable of bending as the instrument is maneuvered into position. If this structure is flexible, there are fewer constraints on its configuration. The electrically conductive structure may be configured as a half wavelength resonator or as a quarter wavelength resonator.

At least one of the inner or outer conductors may be made from silver. The thickness of the inner and outer conductors may be no more than 50 microns, and preferably no more than 25 microns, and most preferably no more than 10 microns. These thicknesses are sufficient for transmission of microwave energy along the coaxial transmission line but are as small as possible in order to maximize the size of the hollow defined by an inner surface of the hollow inner conductor.

The needle preferably has a diameter of no more than 1 mm, and more preferably no more than 0.5 mm, in order to fit through the liquid channel, and also to minimize the amount of space required for the needle. In some embodiments the diameter of the liquid channel may be substantially the same as the diameter of the needle in order to achieve a tight fit between the two. Although the primary purpose of the liquid channel and needle is to deliver liquid to a treatment site, it may be possible for a gas to be delivered through the liquid channel, e.g. to flush the needle. In some circumstances, gas may be delivered through the needle at the same time as applying microwave energy. It may be possible for the microwave energy to strike a plasma from the gas in this situation. This example may provide an additional plasma source which is more focussed than that used in the plasma generating mode discussed above.

Broadly speaking, the electrosurgical instrument has three main modes of operation:

(i) Liquid administration mode, where liquid from the liquid channel is administered to a target area via the aperture in the probe tip.

(ii) Non-ionising radiation mode, where the conducting structure formed by the first and second electrodes acts as a radiating antenna structure to emit RF and/or microwave EM energy into the surrounding biological tissue.

(iii) Plasma-generating mode, where the RF energy is used to generate an electric field between the first and second electrodes which strikes a plasma in a gas which is passed over and/or between the first and second electrodes, and where the microwave energy is supplied to sustain the plasma.

A second aspect of the invention provides an electrosurgical apparatus for performing coagulation having: a microwave signal generator for generating microwave EM energy; a radiofrequency (RF) signal generator for generating RF EM energy having a frequency lower than the microwave EM frequency; an electrosurgical instrument as described above connected to receive the microwave/RF EM energy; a feed structure for conveying the microwave/RF EM energy to the probe, the feed structure including a microwave channel for connecting the coaxial transmission line to the microwave signal generator and an RF channel for connecting the coaxial transmission line to the RF signal generator, a gas feed connected to supply gas to the electrosurgical instrument, and a liquid feed connected to supply liquid to the electrosurgical instrument, wherein the apparatus is operable: in a plasma-generating mode for surface coagulation, whereby the microwave EM energy and RF energy delivered to the probe tip are arranged to strike and sustain a gas plasma between the first and second electrodes; and in a non-ionising radiation mode, whereby the microwave EM energy delivered to the probe tip is arranged to emit a non-ionising EM field outwardly from the probe tip for tissue coagulation; and in a liquid administration mode, whereby liquid is supplied to a target area via the liquid feed, the liquid channel and the aperture at the distal end of the probe tip channel.

In a preferred embodiment, there is a mechanism in place for ensuring that only one of the above three operating modes is active at any given time. In addition, it is preferred that all three modes are readily available, so that switching between them can be effected quickly. Having a needle which is adjustable, so that it can be located in the retracted position when it is not necessary to administer a liquid, can ensure that the needle is not exposed during periods when the instrument is in microwave emission mode or plasma generation mode. Preferably, the instrument includes a locking mechanism to physically restrict the use of microwave emission mode or plasma-generation mode while the needle is in the exposed position. This may include a switch mechanism, which is configured so that an electrical connection which is necessary for microwave emission or plasma generation is only made when the needle is in the retracted position. Preferably, no power is delivered to the probe tip while the needle is in the exposed position.

For example, in one embodiment, in order to prevent emission of a microwave field when the needle is in the exposed position, the inner conductor of the coaxial transmission line may have an axial gap, and the needle or the needle adjustment means may include a conducting ring, arranged to bridge the axial gap in the inner conductor when the needle is in the retracted position. When the needle is moved into the exposed position, the conducting ring also moves so as no longer to bridge the gap in the inner conductor, breaking an electrical connection, and thus power is not delivered to the probe tip, preventing emission of the microwave field.

The apparatus may also operate in a RF coagulation mode, where RF energy is applied between the first electrode and second electrode to coagulate tissue. The RF coagulation mode may be used before the non-ionising radiation mode, i.e. while the impedance of the tissue is still at a relatively low level.

The RF energy may be supplied with the microwave energy in the non-ionising radiation mode in order to augment the coagulation effect. It has been found that sustained RF delivery, e.g. for over 6.5 seconds, leads to a large increase in the impedance at the tip of the instrument. Then, the electrosurgical instrument behaves like a hot poker, delivering energy only to the tissue immediately adjacent to the tip, rather than at a desirable depth. In order to address this issue, when operating in the non-ionising radiation mode, the instrument described herein may operate to switch from RF to microwave energy delivery when the impedance of the tip reaches a predetermined threshold, such as 200Ω.

There may be a plurality of selectable operation schemes for the non-ionising radiation mode, as follows:

1) For shallow coagulation, only RF energy may be delivered for 1 to 2 seconds. This may be useful in lower gastrointestinal procedures.
2) For medium-depth coagulation, only microwave energy may be delivered, for example at 10 W, for 2 to 6 seconds.
3) For deeper coagulation, a scheme in which sequence 1 followed by sequence 2 above may be used. Deeper coagulation is possible in this way because the effect of the microwaves is enhanced when there is less absorption in the tissue immediately adjacent to the tip. The change from sequence 1 to sequence 2 may also be prompted when a threshold impedance at the tip is detected. Alternatively, the change may be prompted by detecting when more power would be delivered using microwave energy than RF energy, e.g. when the RF power falls below 10 W. This sequence may be useful for upper gastrointestinal bleeds.

Another, more complex sequence of treatment may be employed, for example:

Time slot 1: 100% RF energy
Time slot 2: 20% microwave energy, 80% RF energy
Time slot 3: 40% microwave energy, 60% RF energy
Time slot 4: 80% microwave energy, 20% RF energy
Time slot 5: 100% microwave energy.

Additionally combining RF with microwave energy or interspersing the microwave and RF energy may be beneficial for other procedures such as tumour ablation.

The electrosurgical apparatus may include an impedance transformer structure, for ensuring impedance matching between the coaxial transmission line and the feed structure to ensure optimum power delivery.

The impedance transformer structure may include: a signal generator input feed for receiving signals from the RF/microwave signal generator; a transformer output arranged to deliver signals to the coaxial transmission line of the electrosurgical instrument; and an impedance matching section located between the signal generator input feed and the transformer output, having an impedance and dimensions selected to match the impedance between the input port and the output port. The impedance of the impedance matching section is preferably selected by calculating the geometric mean of the impedances of the signal generator input feed and the coaxial transmission line of the electrosurgical instrument, and preferably has a length equal to an odd multiple of (e.g. 1, 3 or 5 time) a quarter of the wavelength of the microwave energy received at the signal generator input feed (herein "a wavelength" is used to refer to the wavelength provided by the signal generator, unless context clearly dictates otherwise).

Preferably, the impedance transformer structure includes a hollow channel, having a liquid/gas input port at one end, and which meets the impedance matching section at the other end, the hollow channel configured to deliver liquid and gas to the liquid channel and gas channel of the electrosurgical instrument of the present invention, via the impedance matching section. The impedance matching section is preferably in the form of an impedance matching coaxial transmission line.

The hollow channel, the impedance matching section and the signal generator input feed may all meet at a junction, and if so the distance between the junction and the transformer output is preferably one quarter of a wavelength (or an odd multiple thereof).

A choke structure may be located on the hollow channel, in order to ensure that microwave energy does not pass along the hollow channel, and more specifically, to ensure that microwave energy which enters the impedance transformer structure is only able to propagate along the impedance matching structure. The choke structure may include a circular air gap all the way around the hollow channel, arranged to force an open circuit. The plane of the circular air gap is preferably perpendicular to the longitudinal axis of the hollow channel at the point of the air gap, although it may have a stepped or staggered edge to minimise the increase to the instrument outer diameter. The air gap may have a length equal to an odd number of quarter wavelengths. The choke structure is preferably located a distance of half a wavelength from the junction. More preferably, the hollow channel includes a second circular air gap located half a wavelength from the first, in the opposite direction to the junction.

The choke structure enables the instrument to be configured as an open circuit at the proximal end, which allows RF energy to be delivered.

The electrosurgical instrument may be connected to the feed structure, the gas feed and the liquid feed via a handpiece, which is manually operable by a user of the electrosurgical apparatus. The impedance transformer discussed above, if required, may be part of the handpiece. However, if the feed cable has the same characteristic impedance as the generator (e.g. 50Ω), no transformer is needed.

The apparatus may comprise a strike signal generation circuit arranged to cause a pulse (or pulses) of RF EM energy to be delivered to the probe tip to generate the high electric field between the first electrode and the second electrode across the gas flow path for striking the plasma, wherein the strike signal generation circuit includes control circuitry arranged to use a detectable characteristic of a pulse of microwave EM radiation on the microwave channel to trigger generation of the pulse of RF EM radiation. The RF EM radiation is thus used to strike the plasma, whereas the microwave EM radiation is used to sustain the plasma. By coordinating the delivery of an RF strike pulse with a pulse of microwave EM radiation as described above, the apparatus is capable of striking the plasma with greater certainty.

While the instrument may be arranged to generate a thermal plasma, it may also be arranged to generate a non-thermal plasma for sterilization. In the coaxial plasma-generating arrangement described above, where the inner diameter of the first electrode within the coaxial arrangement has a diameter of between 3 mm and 5 mm, and a quartz tube that fits tightly inside with a wall thickness of between 0.25 mm and 1 mm, and where the outer diameter of the second electrode is between 0.75 mm and 4 mm (allowing a space for gas to flow in the region between the inner conductor and the inner wall of the quartz tube), that a non-thermal plasma suitable for disinfection or sterilisation can be produced by operating the generator in pulsed mode with a duty cycle of less than 40%, i.e. 28%. In one embodiment, the rms power in a single microwave pulse is 50 W and the pulse ON time is 40 ms, within a total period of 140 ms, i.e. the average power delivered into the plasma is 14.28 W at 2.45 GHz. When an RF strike pulse is used in this configuration, the duration of the RF strike pulse is around 1 ms, and the frequency of the sinusoidal oscillations was 100 kHz. The amplitude was around 1 kV peak (707 Vrms). The RF power was less than 10% of the microwave power. The RF pulse was synchronised to the microwave burst or pulse and triggered on the rising edge of the microwave burst or pulse.

To produce thermal plasma, the duty cycle may be increased, i.e. to 50% or continuous wave (CW) and/or the rms power level may be increased, i.e. to 75 W or 100 W for this particular applicator geometry (if the geometry decreased or increased then the microwave power and the amplitude of the RF strike pulse would be adjusted accordingly). The ratio of RF to microwave power will preferably remain constant, i.e. less than 10%, and possibly equal to or less than 1%, for non-thermal and thermal plasma.

Having the ability to perform sterilisation at the distal end of the instrument may be particularly advantageous for the purpose disinfecting the instrument channel of scopes. In order words, the non-thermal plasma is emitting as the instrument is withdrawn from the scope (e.g. endoscope or the like) to treat the inner surface of the instrument. Whilst non-thermal plasma is preferred for this process, it may also be possible to achieve sterilisation by delivering non-ionising microwave or RF radiation only, i.e. in the absence of gas.

The sterilising function of the non-thermal plasma may also be used to sterilise body cavities before or after treatment. Where the device is used to clean or sterilise instruments, e.g. endoscopes or gastroscopes, the device may be configured to produce a combination of non-thermal plasma and non-ionising microwave radiation. The device may also be configured to produce non-thermal plasma, thermal plasma and non-ionising microwave radiation where it is used in NOTES procedures or where it is advantageous to be able to perform surface coagulation, sterilisation of body tissue and deep coagulation of large vessels or bleeders.

BRIEF DESCRIPTION OF THE DRAWINGS

Embodiments of the present invention will now be described with reference to the accompanying drawings, in which.

DETAILED DESCRIPTION OF THE EMBODIMENTS

Figure 1A:
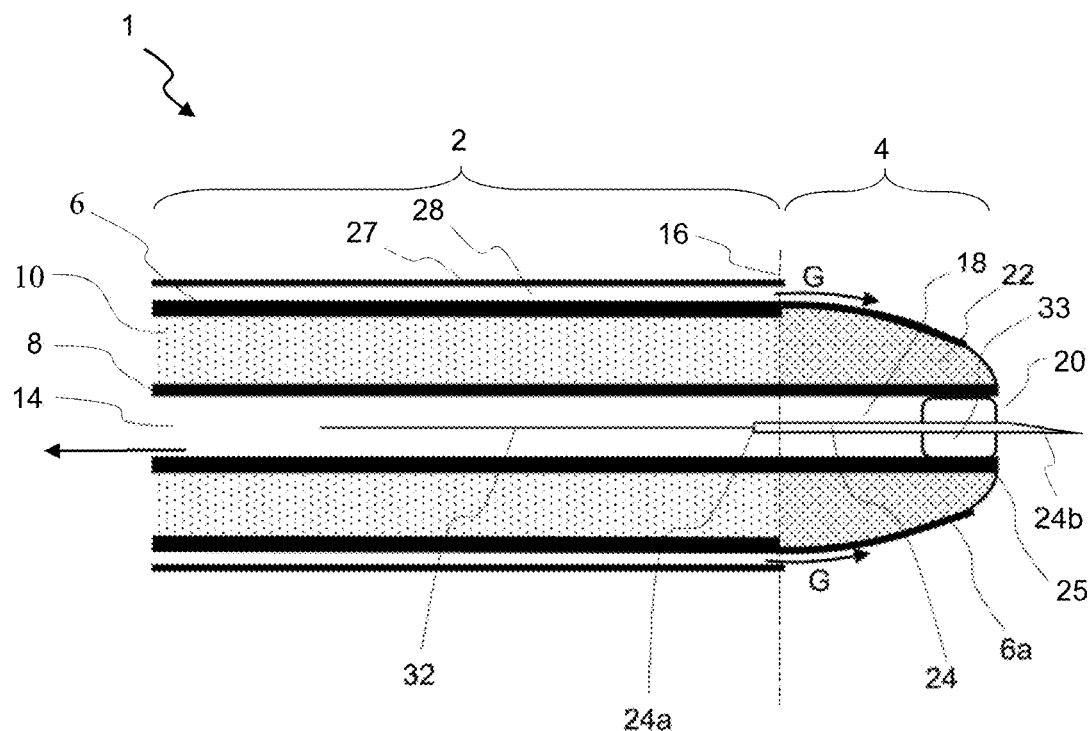
FIG. 1A is a schematic, lengthwise cross-section of part of the coaxial transmission line and probe tip according to a first embodiment of the present invention, with the needle in an exposed position.
Figure 1B:
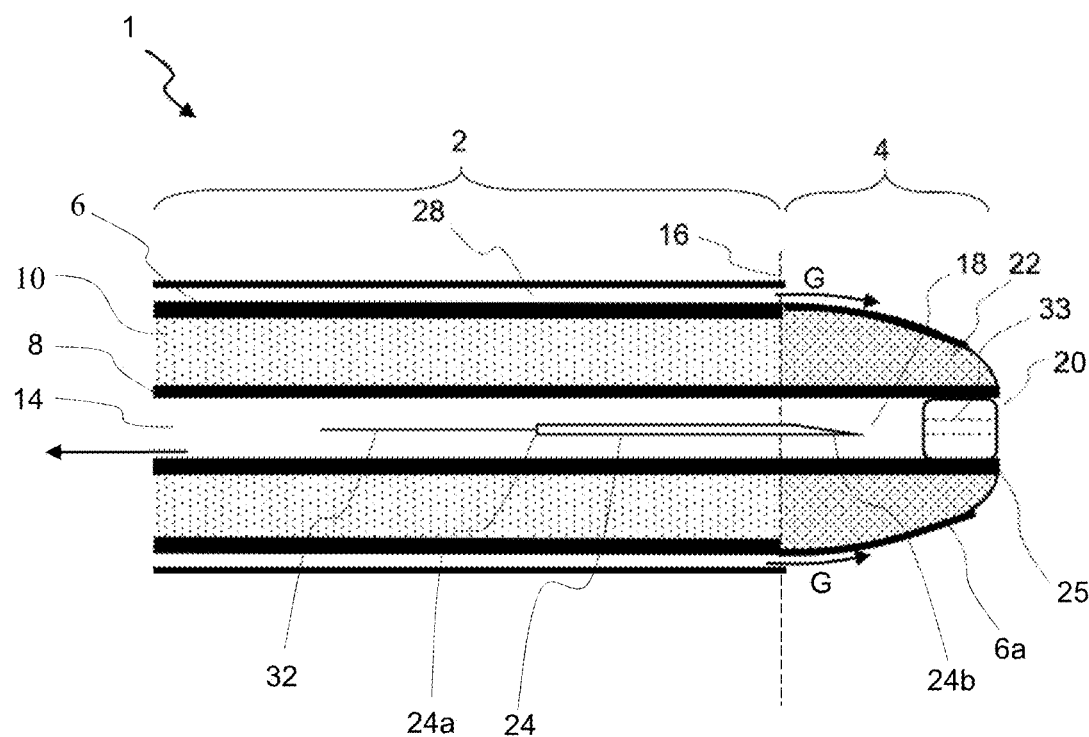
FIG. 1B is a schematic, lengthwise cross-section of part of the coaxial transmission line and probe tip according to a first embodiment of the present invention, with the needle in a retracted position.
Figure 2:
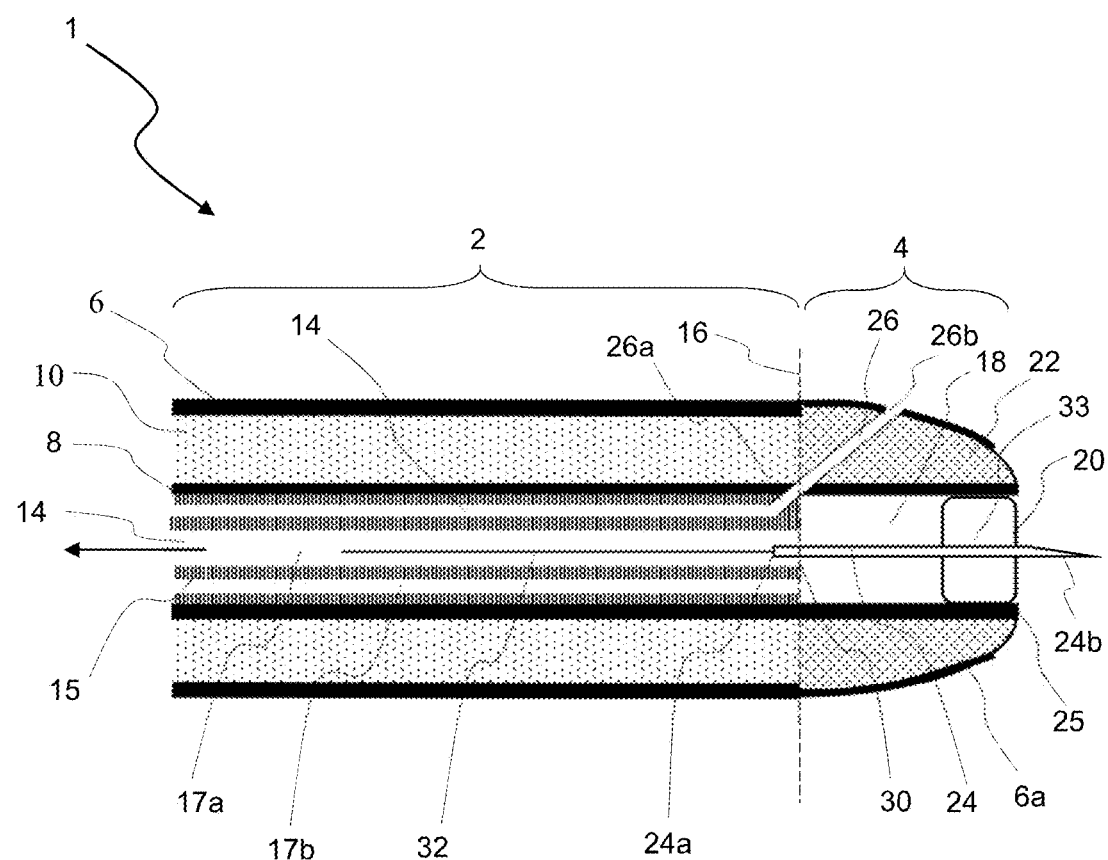
FIG. 2 is a schematic, lengthwise cross-section of part of the coaxial transmission line and probe tip according to a second embodiment of the present invention, with the needle in an exposed position.
Figure 3:
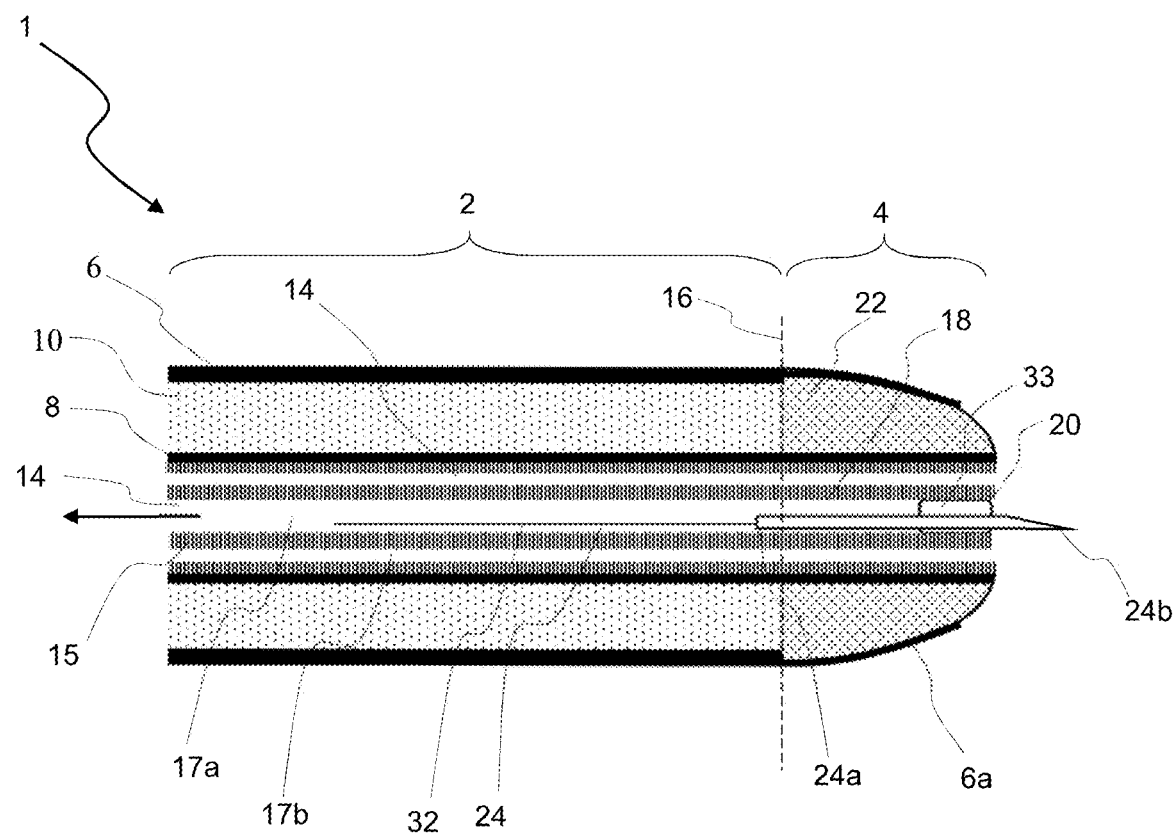
FIG. 3 is a schematic, lengthwise cross-section of part of the coaxial transmission line and probe tip according to a third embodiment of the present invention, with the needle in an exposed position.

FIGS. 1 to 3 show lengthwise cross sections of different embodiments of the present invention, which present different configurations by which the gas may be provided to the region between the first and second electrodes, in order that a plasma may be struck between the electrodes in the presence of a high electric field. FIGS. 5 to 7b show various arrangements of conducting material on the probe tip which form the radiating antenna structure and the first and second electrodes in different embodiments of the present invention. It is noted that these probe tip arrangements may be employed with any of the gas delivery structures shown in FIGS. 1 to 3.

FIG. 1A shows a lengthwise cross section of a part of a coaxial transmission line 2, and a probe tip 4, joined at an interface 16. The coaxial transmission line 2 receives microwave and/or RF input from a feed structure (not shown) to the left of the drawing, as shown by the arrow. Liquid (e.g. adrenaline or saline) is also fed into the coaxial transmission line from the same direction. The coaxial transmission line 2 is defined by an outer conductor 6, and a hollow cylindrical inner conductor 8, both formed of a conducting material such as silver. A first dielectric material 10 separates the outer conductor 6 from the inner conductor 8 both spatially and electrically. The inner surface of the inner conductor 8 defines a channel 14. On the outer surface of the outer conductor 6 is an outer jacket 27, which is spaced from the outer surface of the outer conductor 6. This spacing may be maintained by using spacers between the jacket 27 and the outer surface of the outer conductor 6. The space defined by the jacket 27 and the outer conductor 6 forms the gas channel 28 in the present embodiment. At a proximal end of the gas channel 28, a gas source such as an argon source is connected, to supply gas to the gas channel 28. The distal end of the gas channel 28 is situated at or near the interface 16 of the probe tip 4 and the coaxial channel 2. Gas exiting the channel then flows over the outer surface of the probe tip 4, as shown by the arrows G.

Figure 4A:
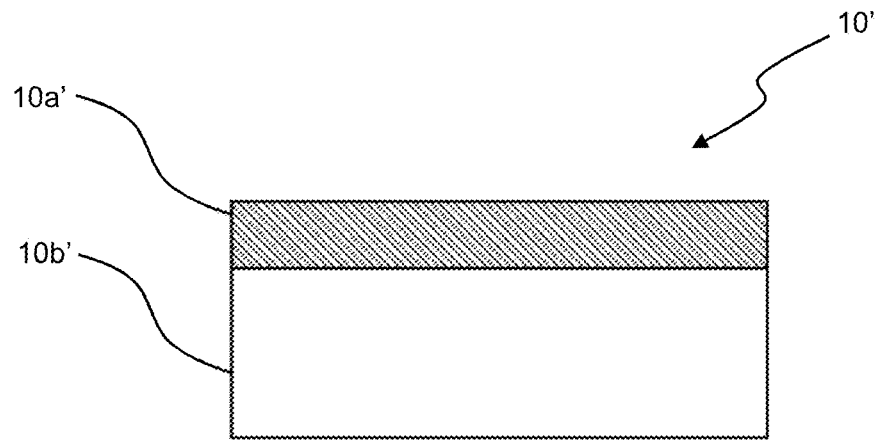
FIGS. 4A and 4B are schematic diagrams of a multi-layered dielectric structure which may be used in the coaxial transmission line in all embodiments of the present invention.
Figure 4B:
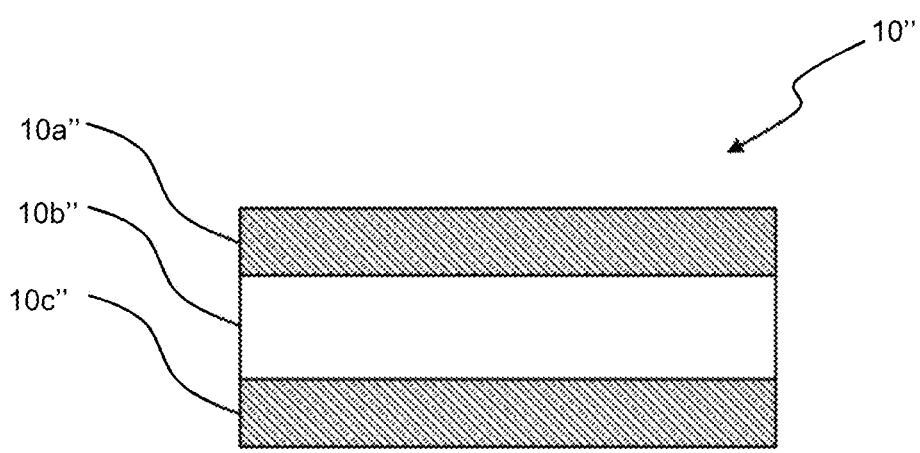

Instead of being made up of a single material, alternative structures for the dielectric material 10 are shown in FIGS. 4A and 4B. In FIG. 4A, the dielectric material 10' is a dual-layered structure. Layer 10a' is a thin layer of dielectric material having a high dielectric strength (i.e. a high breakdown voltage), and layer 10b' is a thicker layer of dielectric material that exhibits low dielectric loss (i.e. has a low tan 5). In combination the layers enable propagation of microwave EM energy with low loss whilst providing protection against breakdown when RF energy is supplied. FIG. 4B shows a triple-layered structure for the dielectric material. In FIG. 4B, thin layers 10a", 10c" are made up of a dielectric material having a high dielectric strength, and thicker layer 10b" is made up of a lower dielectric strength and lower dielectric loss material. The layers 10a" and 10c" may be made of the same dielectric material, but may also be made of different dielectric materials. The arrangements shown in FIGS. 4A and 4B may be used in the coaxial transmission lines of any of the embodiments shown in the drawings.

Probe tip 4 is connected to the coaxial transmission line 2 at the interface 16. The probe tip 4 has a second dielectric material 22, which is formed into a cylindrically-symmetrical dome shape, with a central probe tip channel 18 running along its axis of symmetry. The rightmost end of the probe tip channel 18 defines an aperture 20. The inner conductor 8 is longitudinally extended into the probe tip channel to form the first electrode, which is in the form of a conducting shell on the inner surface of the probe tip channel 18. At the distal end of the probe tip channel 18, the end surface of the conducting shell 25 is exposed to the target area.

A hypodermic needle 24 is located inside the liquid channel 14. Needle 24 has a first end 24a and a second end 24b. A rigid guide wire 32 is attached to the first end 24a of the needle 24. The guide wire 32 is used to move the needle 24 left and right, in the view of FIG. 1A, i.e. forwards and backwards along liquid channel 14. A plug 33 is located in the aperture 20 of the probe tip channel 18. The plug 33 is resilient deformable to enable formation of a fluid tight seal with the inner surface of the conducting shell. Plug 33 has an aperture running through it, through which needle 24 can be passed. When the needle 24 passes through plug 33, and the second end 24b of the needle 24 protrudes from the plug 33, and in use, is thus exposed to the target area of biological tissue. The needle 24 is then in an exposed position. In this position, when a liquid is fed to the first end 24a of the needle 24, via the liquid channel 14, it can exit through the second end 24b of the needle to the surrounding area, for treatment or otherwise.

The guide wire 32 can be used to draw the needle 24 from the position depicted in FIG. 1A, to the position shown in FIG. 1B. In FIG. 1B, the needle 24 is withdrawn such that the second end 24b of the needle is situated inside the liquid delivery region 28 of the probe tip 18, and is therefore no longer exposed to the surrounding area. This is the retracted position. When the needle 24 is in this position, the resiliently deformable nature of the plug 33 ensures that it seals itself, preventing liquid inside the probe tip channel 18 from escaping to the surroundings, and preventing liquid or other matter from the surroundings from entering the probe tip channel 18, and contaminating its contents. The plug may include a one-way valve that permits passage of the needle. The needle may also include a one-way valve to inhibit back flow into the liquid channel. From the retracted position of needle 24 shown in FIG. 1B, the guide wire 32 may be used to push the needle back through the plug 33 to return it to the exposed position depicted in FIG. 1A.

In use, in a plasma-generating mode, RF energy from the coaxial transmission line 2 is received at the probe tip 4. An electric field is thus generated between the exposed surface of the conducting shell 25, and the outer conductor 6. Therefore, when gas exits the gas channel 28, as shown by the arrows G, because it is in the presence of the electric field generated between the end surface of the conducting shell 25, and the outer surface of the outer conductor 6, which respectively constitute the first and second electrodes, a plasma may be struck across the outer surface of the probe tip 4. The outer conductor 6 may having one or more distally extending elements or fingers 6a which extend over part of the surface of the dielectric material 22 towards the conducting shell 25. There may be two of more fingers, with a gap of exposed dielectric surface between each pair of adjacent fingers. These features have the effect of decreasing the gap between the first electrode and second electrode in certain areas on the probe tip. This increases the strength of the electric field in this areas to create regions of preferential ionisation. The gap between the first and second electrodes in these regions may be less than 0.5 mm. The extending elements or fingers may have any shape.

FIG. 2 shows an alternative embodiment. The structure of the coaxial transmission line 2 and the probe tip 4 are the same however, in the embodiment shown in FIG. 2, there is additionally a multi-lumen structure 15 located inside the liquid channel 14. The multi-lumen structure 15 consists of an elongate cylindrical piece of flexible material having several bores running through it. An elongate cylindrical liquid channel 17a runs along the central axis of the multi-lumen structure 15, and is surrounded by six smaller peripheral gas channels 17b, which are distributed evenly around the liquid channel 17a, and are each identical (see for example FIG. 5). In use, the liquid channel 17a is connected at its proximal end to a source of liquid, such as an adrenaline source, and the gas channels 17b are connected to a source of gas such as argon. In the present embodiment, the outer surface of the multi-lumen structure 15 is flush with the inner surface of the inner conductor 8. The inner surface of the inner conductor 8 may also have a protective coating, but this is not shown in the present drawing. Near the distal end of the multi-lumen structure 15, there is a branch point 26a, where a gas exit channel 26 branches off obliquely from the main gas channel 17b. The gas exit channel 26 passes through the inner conductor 8, part of the first dielectric material 10 and the second dielectric material 22 in the probe tip 4. It may also pass through any distally extending fingers of the outer conductor that are present on the dielectric material 22.

Due to the narrow width of the gas exit channel 26, only a small opening is necessary in the inner conductor 8 and so its ability to convey microwave/RF energy is not compromised. The gas exit channel 26 terminates in a gas exit aperture 26b in the outer surface of the probe tip 4. In this way, rather than exiting the probe tip channel 18 via the aperture 20, gas is able to pass through the gas exit channel 26, and exit via the aperture 26b, allowing the flow path of the gas to be located relatively centrally in the region between outer conductor 6 and the exposed surface of the conducting shell 25.

In use, in a plasma-generation mode, RF energy from the coaxial transmission line 2 is received at the probe tip 4. An electric field is thus generated between the exposed surface of the conducting shell 25, and the outer surface of the outer conductor 6. The gas (e.g. argon) exits the gas exit channel 26, via the aperture 26b, into the region of high electric field, and thus, a plasma may be struck at the probe tip 4. Microwave EM energy is supplied to sustain the plasma.

FIG. 3 shows another alternative embodiment of the present invention. This embodiment differs from those shown in previous drawings in the structure of the gas channel/liquid channel arrangement. Like the embodiment of FIG. 2, this embodiment also includes a multi-lumen structure 15 in the channel 14 defined by the inner surface of the inner conductor 8. Again, as in FIG. 2, the multi-lumen structure 15 includes a plurality of bores, including a central liquid channel 17a and a plurality of peripheral gas channels 17b (see e.g. FIG. 5). In this embodiment, both the multi-lumen structure 15 and the inner conductor 8 extend past the interface 16 all the way to the end of the probe tip 4, also terminating at aperture 20. A hypodermic needle 24 is located in the liquid channel 17a, and has a first end 24a and a second end 24b. Like the embodiments previously described, a plug 33 is present in the liquid channel 17a, in order to stop backflow of liquid back into the liquid channel 17a, and also stop liquid escaping into the target area when the needle is in a retracted position (not shown). It is noted that other embodiments exist wherein the liquid channel 17a has substantially the same diameter as the hypodermic needle 24, so that the outer surface of the needle 24 lies flush with the inner surface of the liquid channel 17a. In such embodiments, a plug is not required as the contact between the needle 24 and liquid channel 17a is sufficient to form a watertight seal.

Similarly to previous embodiments, in operation in a plasma-generating mode, RF energy received at the probe tip results in a high electric field being generated between the outer surface of the outer conductor 6 and the exposed end surface 25 of the inner conductor 8, which extends (along with the multi-lumen structure 15) to the end of the probe tip 4. Thus, when gas exits the gas channel 17b in the region of the aperture 20, and flows across the outer surface of the probe tip 4, a plasma may be struck as a result of the high electric field. Microwave EM energy is supplied to sustain the plasma.

All three embodiments described above are also capable of operating in a liquid administration mode. In this mode, liquid is supplied via the liquid channel 17a to the first end 24a of the needle 24. The liquid can then pass through the hollow channel of the needle 24, and exit the needle 24 at its second end 24b, to enter the target area. The needle may be extended to the exposed position in order to deliver the liquid, but it may also be possible for liquid to be delivered (e.g. to flush the treatment site) when the needle is in the retracted position.

In the liquid administration mode, the instrument may be arranged to inhibit or prevent the supply of microwave EM or RF energy to the coaxial transmission line 2.

In a non-ionising radiation mode, when microwave energy (possibly in combination with RF energy) is conveyed via coaxial transmission line 2 to the probe tip 4, the first and/or second electrodes are configured to act as a radiating antenna structure. In the embodiments shown in FIGS. 1 to 3, the portion of the inner conductor 8 which extends into the probe tip 4 is able to act as a cylindrically symmetrical monopolar antenna, which emits a microwave field via the second dielectric material 22. The second dielectric material 22 may form radiator for the microwave EM energy. In one example, the second dielectric material 22 may be configured as a quarter wavelength impedance transformer to match the characteristic impedance of the cable to the impedance of the tissue.

Figure 5:
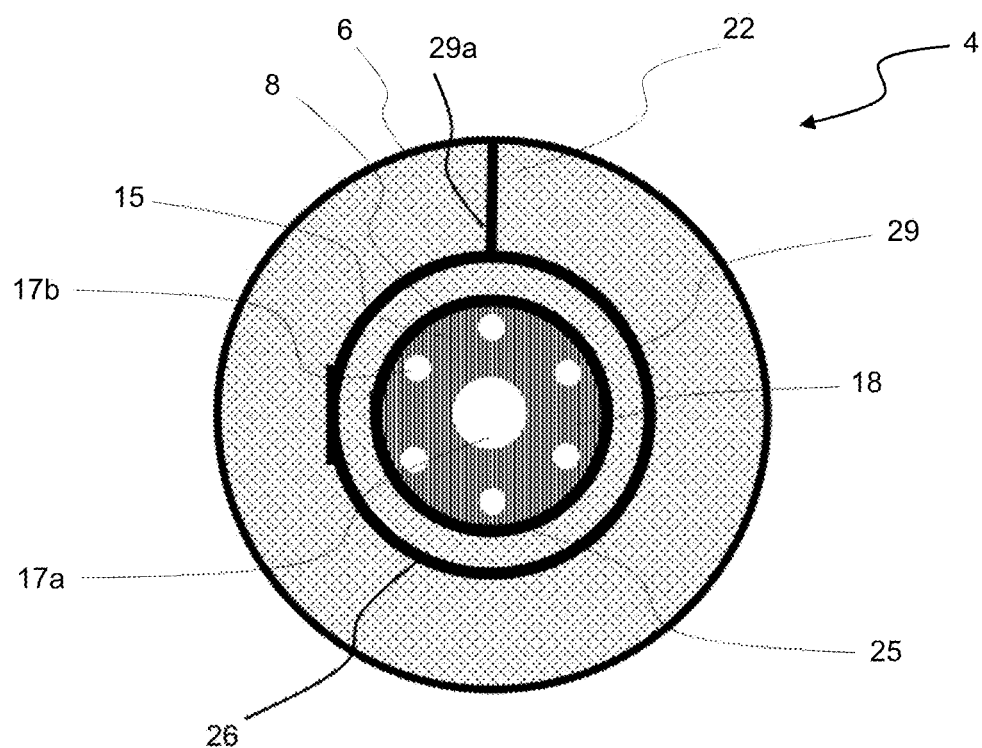
FIG. 5 shows an axial view looking down the probe tip channel of a probe tip configuration which may be employed in embodiments of the present invention.
Figure 6:
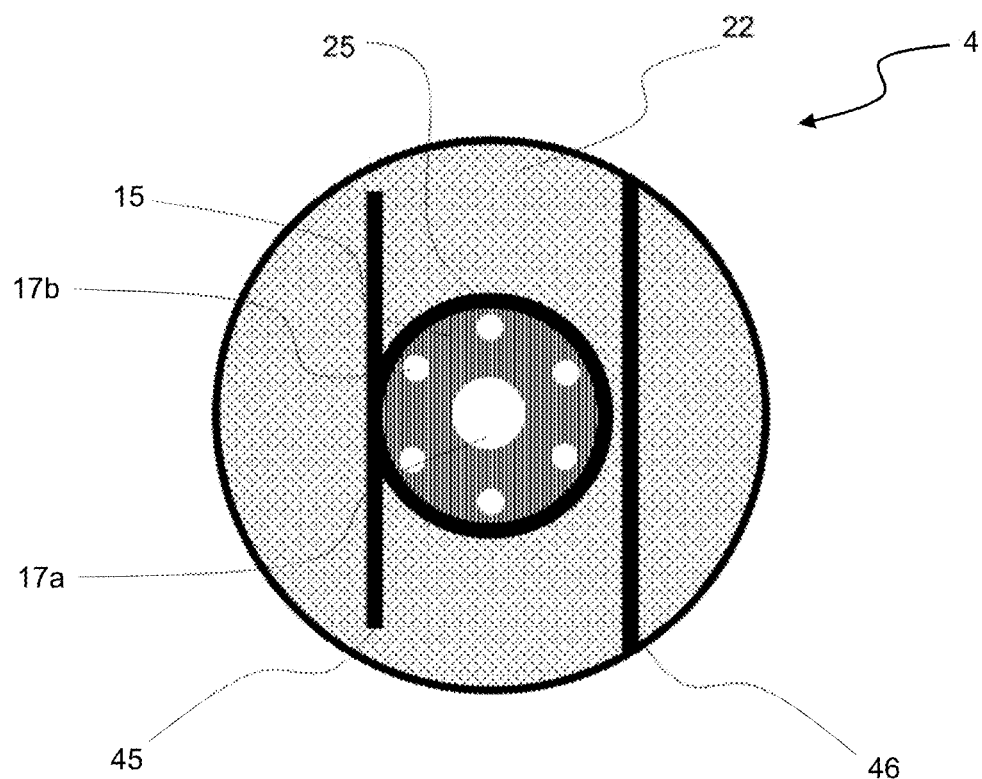
FIG. 6 shows an axial view looking down the probe tip channel of a probe tip configuration which may be employed in embodiments of the present invention.

FIGS. 5 to 7 show arrangements of conducting material on the outer surface of the probe tip 4 which form alternative configurations for the extending fingers of the outer conductor discussed above, which form the first electrode and second electrode.

In FIG. 5, a ring configuration of probe tip 4 is shown, looking down the longitudinal axis of the probe tip channel 18. The distal end of the multi-lumen structure 15 is shown, showing the apertures terminating the central liquid channel 17a and the peripheral gas channels 17b. Surrounding the multi-lumen structure 15 is the inner conductor 8, the exposed surface 25 of which is visible in the present view. This is enclosed by the second dielectric material 22, and the outer conductor 6. Disposed on the surface of the second dielectric material 22 is an additional conductor, in the form of conducting ring 29. Conducting ring 6 is electrically connected to the outer conductor 8 by connecting strip 29a. In this embodiment, the exposed surface 25 of the inner conductor 8 corresponds to the first electrode and conducting ring 26 corresponds to the second electrode.

When RF energy is conveyed to probe tip 4, a high electric field is generated between the exposed surface 25 of the inner conductor 8 and the conducting ring 29. Thus, when gas exits the gas channels 17b and enters the region of high electric field, a plasma can be struck. The ring configuration may equally well be used with the arrangement shown in FIGS. 1A and 1B, wherein the gas channel is formed by a jacket 27 on the outside of the coaxial transmission line 2.

The alternative embodiment shown in FIG. 6 is similar to that shown in FIG. 5 except rather than a ring configuration, the first and second electrodes which form the conducting structure are respectively provided in the form of a first conducting strip 45 and a second conducting strip 46. The first conducting strip 45 is electrically connected to the exposed surface 25 of the inner conductor 8. The second conducting strip 46 is electrically connected to the outer conductor 6. Furthermore, the first conducting strip 45 must be electrically isolated, by means of a gap or otherwise, from the outer conductor 6, in order to prevent a short-circuit between the inner conductor 8 and the outer conductor 6. When RF energy is conveyed to probe tip 4, a high electric field is generated between the first conducting strip 45 and the second conducting strip 46. Thus, when gas exits the gas channels 17b and enters the region of high electric field, a plasma can be struck when it flows back over the outer surface of the probe tip 4. This strip configuration may equally well be used with the arrangement shown in FIGS. 1A and 1B, wherein the gas channel is formed by a jacket 27 on the outside of the coaxial transmission line 2.

In the examples of FIGS. 5 and 6, the radiating antenna structure used in the non-ionising radiation mode is the same as the earlier examples, i.e. a portion of the inner conductor 8 which extends into the probe tip 4 acts as a cylindrically symmetrical monopolar antenna.

Figure 7A:
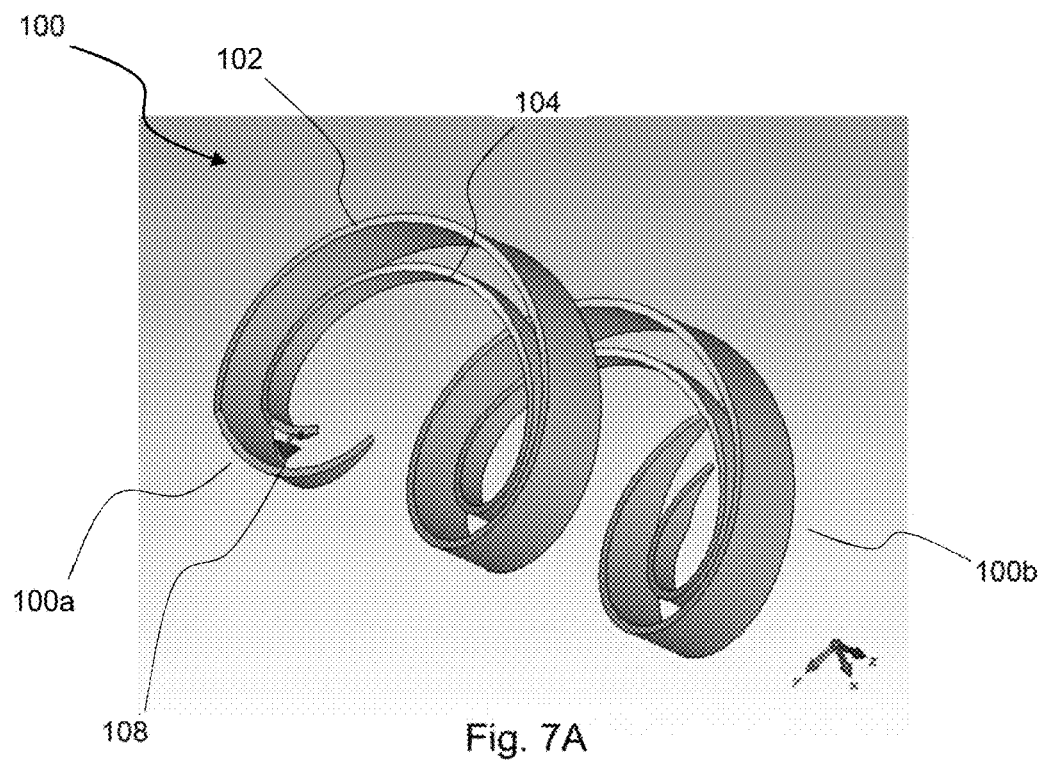
FIG. 7A shows a perspective view of part of a helical antenna which may be used in embodiments of the present invention.

FIG. 7A is a view showing the proximal end of a helical antenna 100, which may form the first and second electrodes, and conducting structure of the present invention. In the drawing, the direction from the proximal end 100a to the distal end 100b of the helical antenna is parallel to the z-axis, as shown in the bottom right corner of the drawing.

A first outer helical electrode 102 and an inner helical electrode 104 are shown in FIG. 6. The inner helical electrode 104 has the same pitch as the first outer helical electrode 102, and has a smaller diameter, so that it runs directly beneath it, and parallel to it. The proximal ends of the two helical electrodes 102, 104 are fed with microwave/RF energy from the coaxial transmission line at the feed point 108, shown by the line and cone. The first outer helical electrode 102 and the inner helical electrode 104, together, form a helical microstrip transmission line, with an impedance of 50Ω (in the presence of an alumina dielectric, see description of drawings below).

Figure 7B:
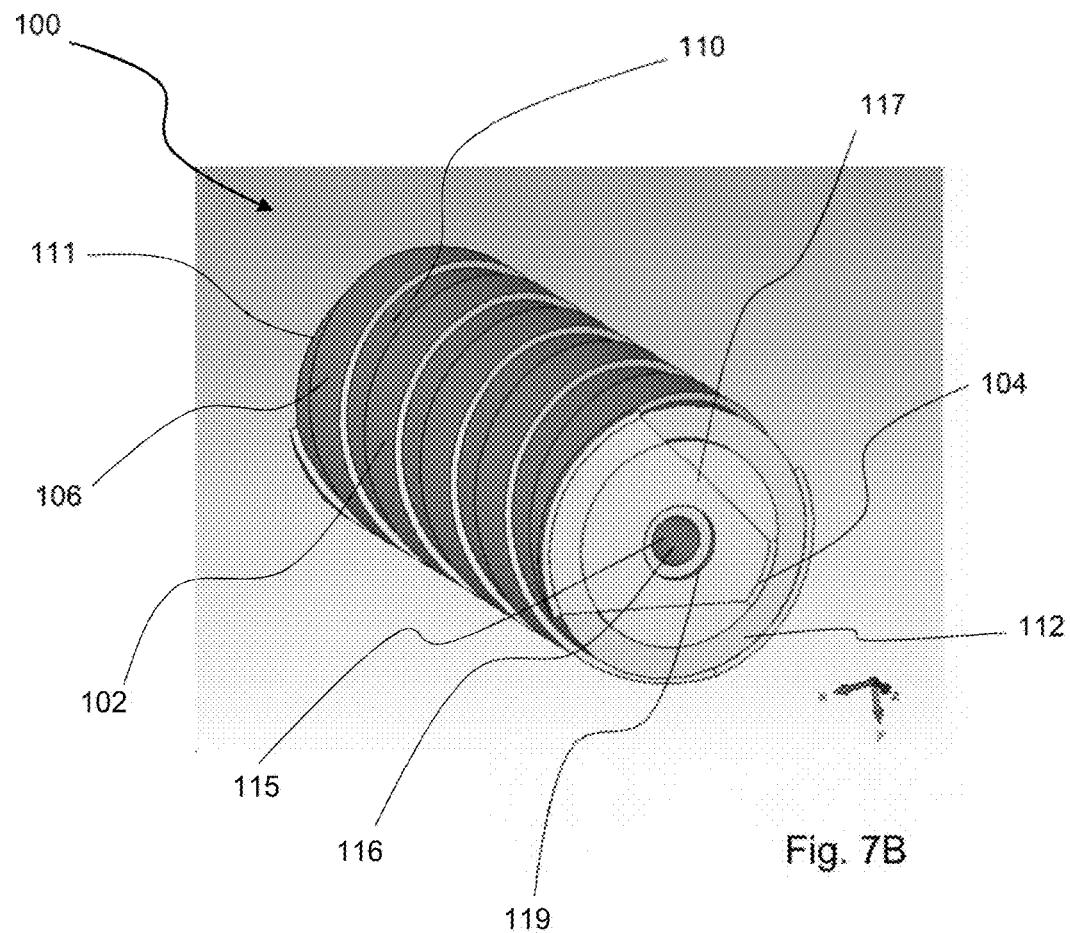
FIG. 7B shows a perspective view of a probe tip which may be used in embodiments of the present invention.

FIG. 7B shows a view of a probe tip 111 having the helical antenna 100 supported thereupon. Probe tip 111 consists of a cylindrical dielectric material 112, which in this case is alumina, having a cylindrical bore through it, forming the probe tip channel 115 which runs from a proximal end to a distal end in the z-direction as shown. The probe tip channel terminates at its distal end with aperture 116. The aperture is unimpeded so that a liquid channel (not shown) or other tool can pass through the probe tip 111 for use on a target area (also not shown).

In addition to the first outer helical electrode 102 and the inner helical electrode 104, a second outer helical electrode 106 is also supported on the dielectric material 112. The second outer helical electrode 106 is diametrically opposite to the first outer helical electrode 102, but has identical pitch. In FIG. 7B, the first and second outer helical electrodes 102, 106 and the inner helical electrode 104 have a pitch of 3.3 mm. Only a distal end surface of the inner helical electrode 104b is visible in FIG. 7B, since inner helical electrode 104 is embedded within the dielectric material 112, running directly beneath the first outer helical electrode 102. At the distal end of the dielectric material 112, the distal end of the second outer helical electrode 106 and the distal end of the inner helical electrode 104 are connected by connecting member 117. The connecting member 117 is a disc shaped piece of conducting material, e.g. copper, which has a hole 119 in the centre to coincide with the aperture 116, in order that it remains unimpeded.

In operation, microwave/RF energy is fed into the proximal end of the helical microstrip transmission line formed by the first outer helical electrode 102 and the inner helical electrode 104. When the microwave/RF energy reaches the distal end, a microwave/RF signal is excited between the first and second outer helical electrodes and propagates along the surface of the antenna. When the probe tip 111 is connected to a coaxial transmission line having a gas channel located around it (not shown) e.g. in a jacket spaced from the coaxial transmission line, the first and second outer helical electrodes 102, 106 and the gaps therebetween 110 lie in the flow path of gas exiting the gas channel. An RF strike pulse causes an electric field to be present between the first and second outer helical electrodes 102, 106 that ionises the gas to generate a plasma. Microwave EM energy is supplied to sustain the plasma.

Figure 8:
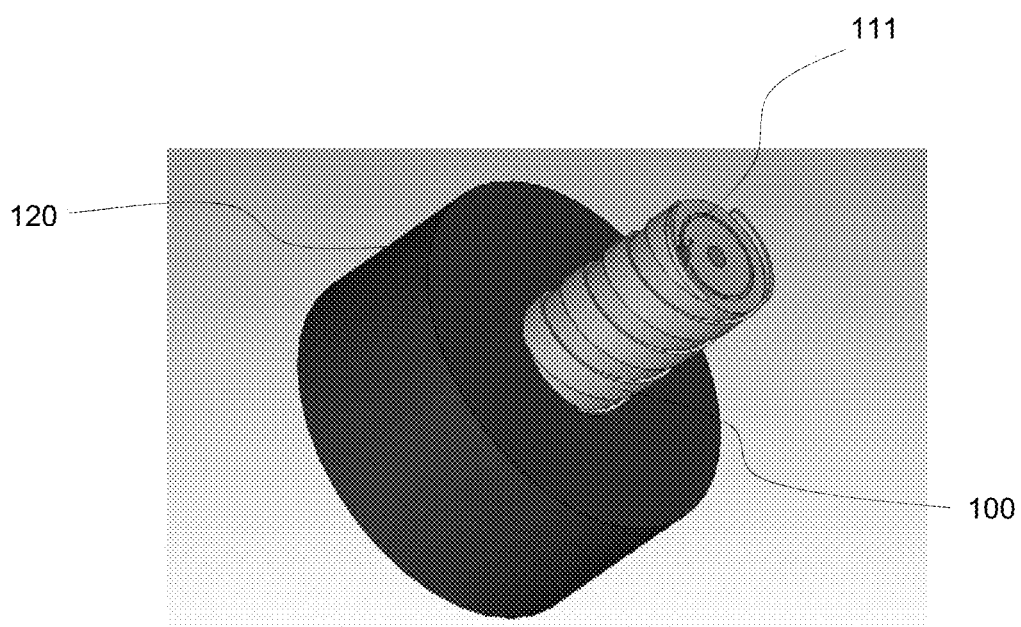
FIG. 8 shows a configuration of a liver load and probe tip which may be used in embodiments of the present invention, which is used to run a simulation.

FIG. 8 shows a model used to simulate the effect of a helical antenna 100 as shown in FIGS. 7A and 7B when placed end-on against a liver load 120. The dielectric material 112 in the model is alumina ceramic, a strong, non-porous dielectric with good dielectric breakdown properties. The dielectric constant is 9.4, and its loss tangent is 0.0004 at 5.8 GHz, which represents a very low loss material at the microwave frequencies employed. A copper helix (i.e. helical antenna 100) was modelled on the outside of a 3.3 mm diameter alumina cylinder which is 7.5 mm long. The pitch of the helix is 3.3 mm, and the width of the copper, measured in a direction parallel to the axis of the cylinder is 0.9 mm. The copper strips in the model shown are 0.1 mm thick, but in practice could be as thin as 0.003 mm. A second copper helix was modelled diametrically opposite (i.e. rotated 180°) from the first copper helix. This resulted in two inter-wound copper helices with a 0.75 mm gap therebetween (in the direction parallel to the axis of the cylinder). The gap may be less than this, e.g. equal to or less than 0.6 mm or equal to or less than 0.5 mm. The gap may vary along the length of the antenna to define zones of preferential ionisation.

The inside diameter of the alumina cylinder (i.e. the diameter of the probe tip channel) was 2.5 mm. A 2.3 mm diameter inner alumina cylinder was modelled inside this, with a 0.6 mm diameter hole in the centre. The hole in the centre may be used to guide a needle (e.g. a 0.5 mm diameter steel needle) or a fibrescope or a miniature surgical tool (e.g. for tissue removal). An inner copper helix was modelled on the inner alumina cylinder which was 0.35 mm wide in the axial direction, and also having a pitch of 3.3 mm. The inner copper helix is located exactly under the centre of the width of one of the outer copper helices.

The distal end of the inner copper helix was connected to the distal end of the copper helix under which it does not directly lie.

The helical antenna made up by the three copper helices was fed with a 50Ω feed at its proximal end, between the inner helix and the first copper helix, and a termination between the proximal ends of the two outer helices. A liver load was created and used to determine the power absorption around the tool. The liver load is representative of a blood load that the device may encounter in normal operation, so this simulation gives an indication of the expected coagulation patterns which may be achieved by using the tool in this way. In the simulation shown, the distal end of the probe tip is inserted 2 mm into the liver load.

Figure 9A:
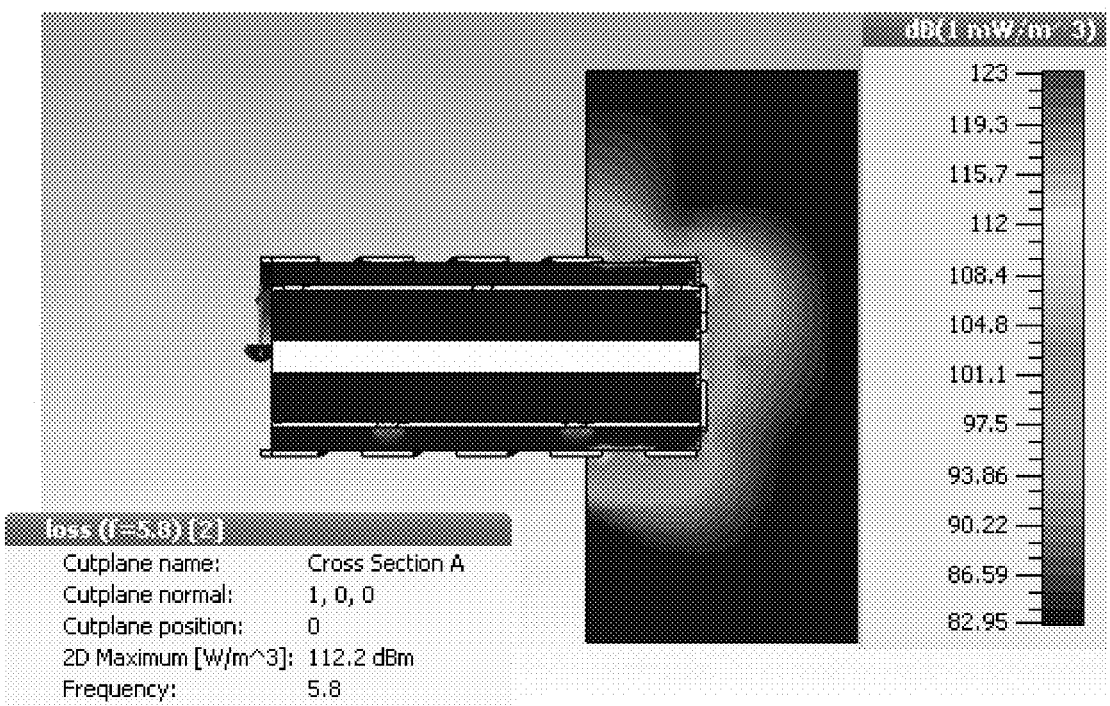
FIGS. 9A to 9D show results of the simulation based on the configuration shown in FIG. 8.
Figure 9B:
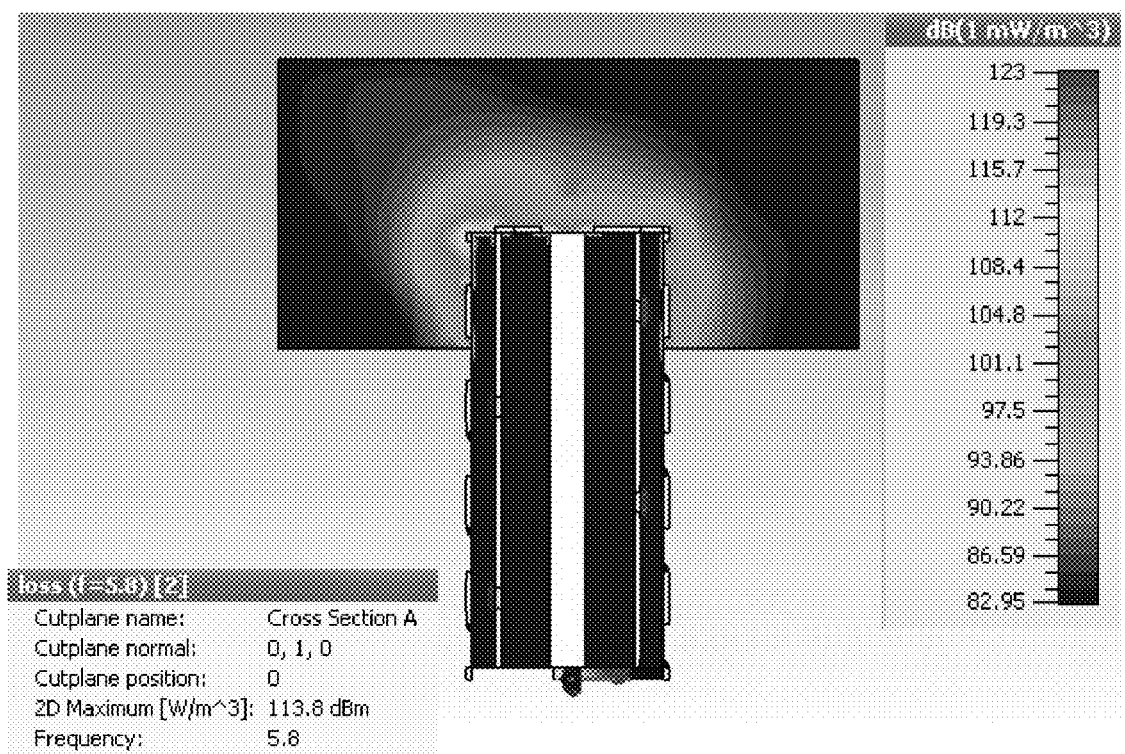
Figure 9C:
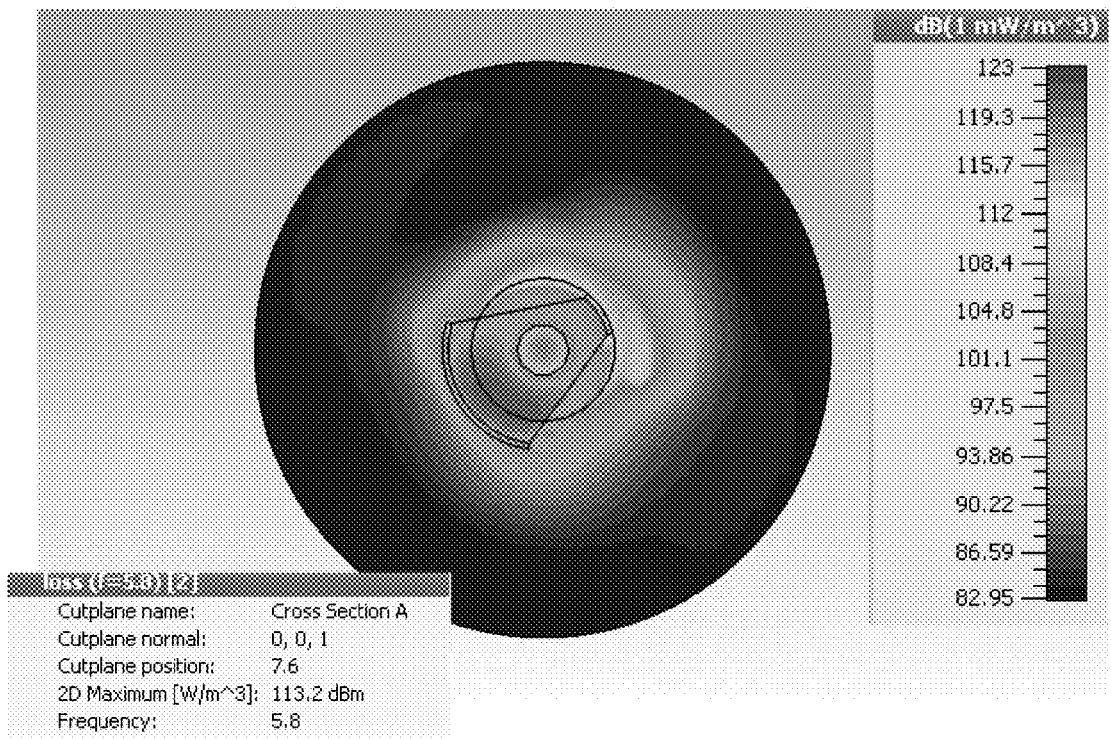
Figure 9D:
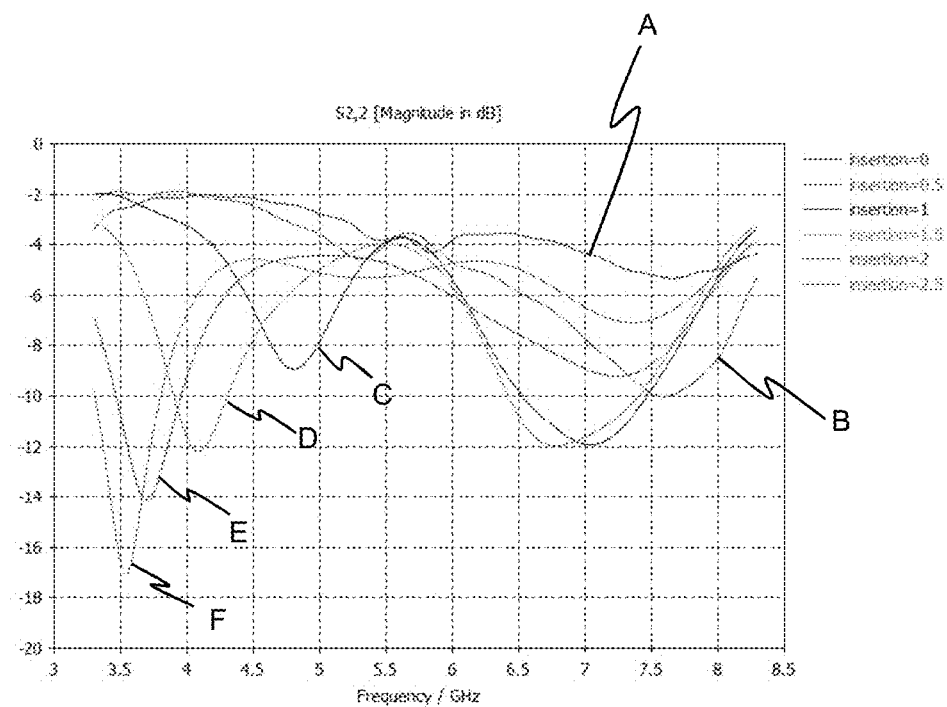

FIGS. 9A to 9C show plots of the power absorption in the liver load around the distal end of the probe tip as shown in FIG. 8 in three different orientations, two taking lengthwise cross sections of the probe tip, and one taking an axial cross section. Overall, these plots show that between 60 and 70% of the microwave power is absorbed into the liver load. FIG. 9D shows the results of simulations of return loss at different penetration depths of the probe tip into the liver load. At 5.8 GHz, it can be seen that the return loss improves from 4 to 5 dB as the insertion increases from 0 (Line A) to 2.5 mm (Line F).

Figure 10:
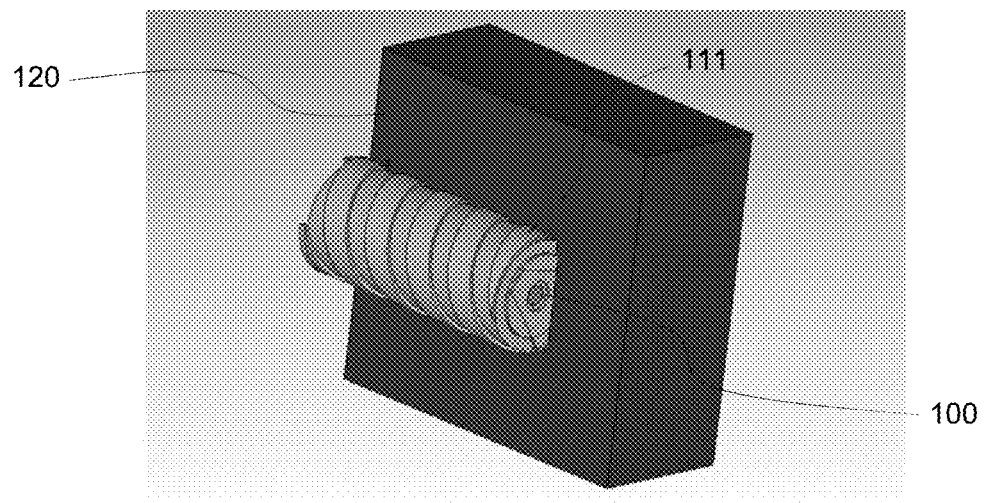
FIG. 10 shows another configuration of a liver load and probe tip which may be used in embodiments of the present invention, which is used to run a simulation.
Figure 11A:
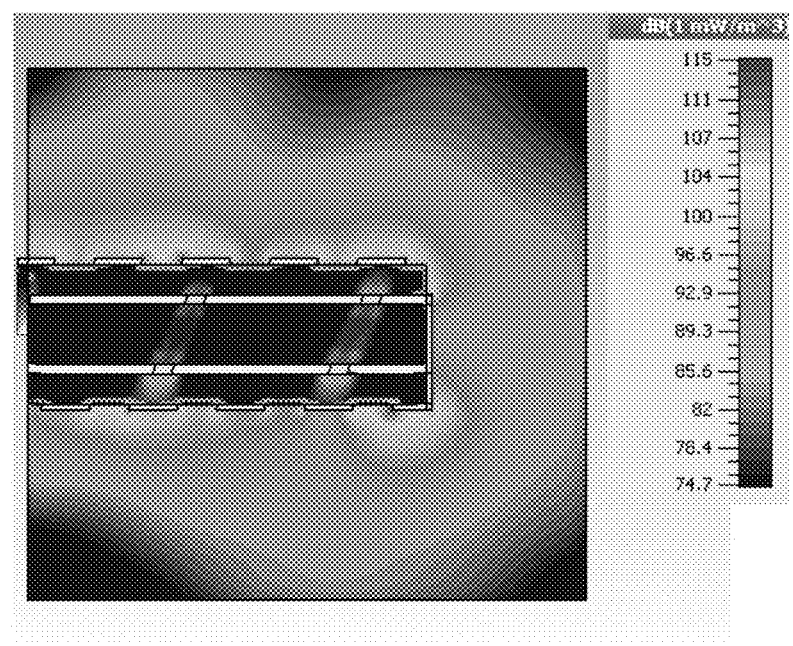
FIGS. 11A to 11D show results of the simulation based on the configuration shown in FIG. 10.
Figure 11B:
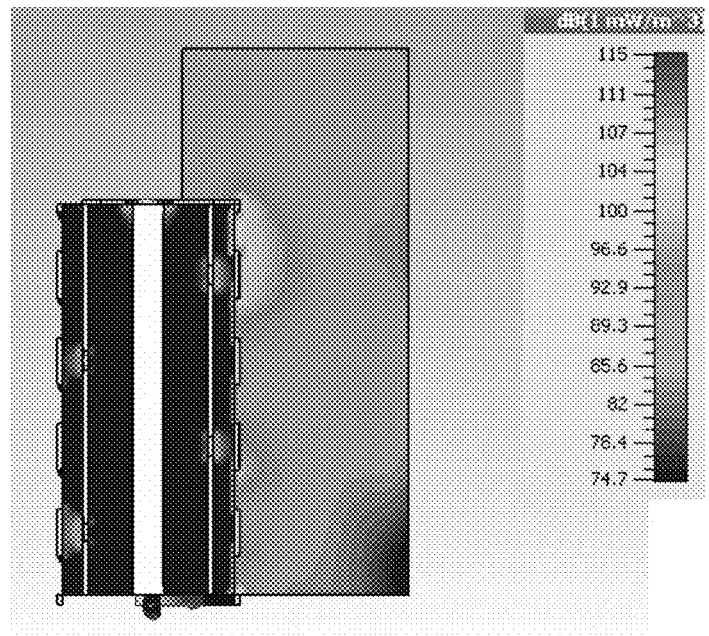
Figure 11C:
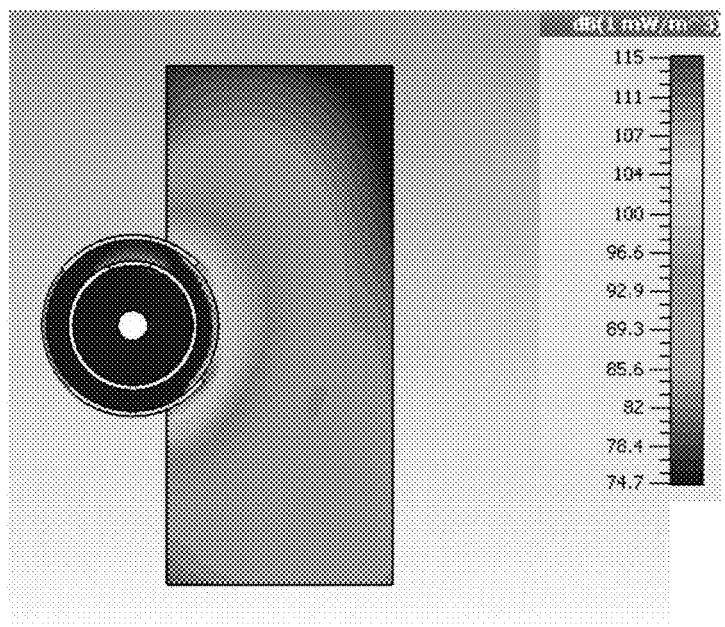
Figure 11D:
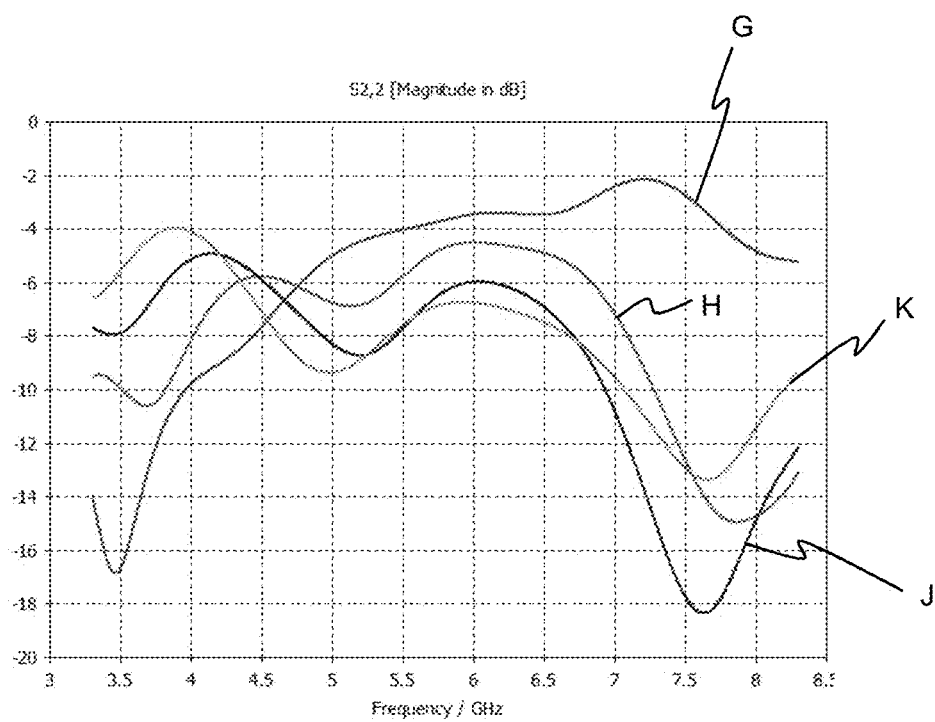

FIG. 10 shows the setup of an alternative simulation, wherein the probe tip is inserted side-on by 1 mm into an identical liver load as in FIG. 8. FIGS. 11A to 11C show plots of the power absorption in the liver load around the probe tip when placed side-on to the liver load. These plots show that the helical antenna is able to produce a substantially even microwave field around the probe tip. FIG. 11D shows the results of simulations of return loss at different penetration depths of the probe tip into the liver load. At 5.8 GHz, it can be seen that the return loss improves from 4 to 7 dB as the (sideways) insertion increases from 0 (Line G) to 1.5 mm (Line K).

The results from the side-on and end-on placement of the helical antenna 100 show that the helical antenna 100 is able to operate effectively as a microwave emitting antenna structure, in addition to being able to strike and sustain a plasma in the helical gaps between the first and second outer helical electrodes.

Figure 12A:
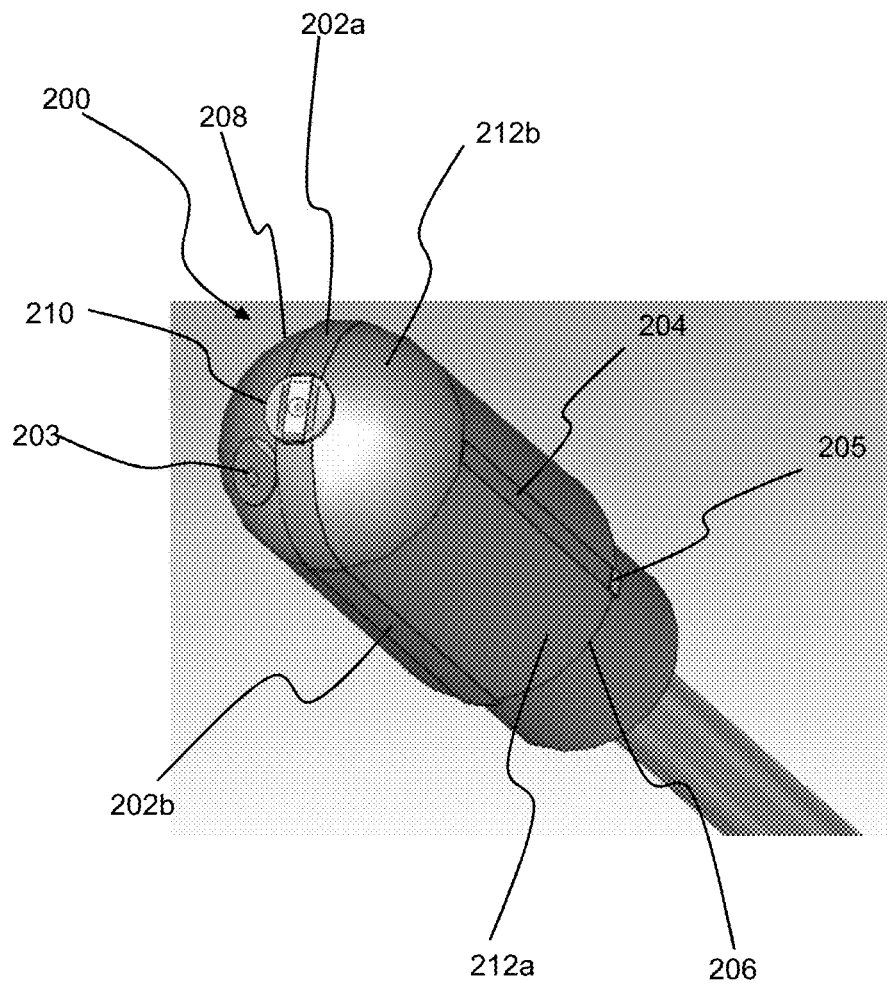
FIGS. 12A-D show an alternative configuration of the probe tip, according to another embodiment of the present invention, and plots of power absorption when that probe tip is placed side-on to a liver load.

FIG. 12A shows an alternative arrangement for the probe tip 200. The first electrode in this arrangement consists of a first conducting strip 202 which includes a first limb 202a and a second limb 202b. The probe tip 200 is made up of a cylindrical section 212a and a hemispherical section 212b. Conducting strip 202 is wrapped around the probe tip 200 to go from its proximal end 206, along the side of the cylindrical section 212a, over the hemispherical section 212b, via the distal end of the probe tip, and symmetrically back over the other side. At the distal end 208 of the probe tip 200, the conducting strip in electrically connected via conductive structure 210 to the outer conductor of the coaxial transmission line. Second conducting strip 204 forms part of the second electrode. The second conducting strip 204 is located on the cylindrical portion 212a only of the probe tip 200. The second conducting strip 204 is located at a position which is 90 degrees removed from both the first limb 212a and the second limb 202b of the first conducting strip 202 so as to bisect the curved region of the outer surface of the probe tip 200 situated therebetween. Though not visible in FIG. 12A, the second electrode also includes a third conducting strip which is situated opposite the second conducting strip 204, so as to bisect the region between the first and second limbs 202a, 202b of the first conducting strip 202 on the opposite side of the probe tip 200. A needle channel 203 also runs longitudinally along the probe tip 200.

Figure 12B:
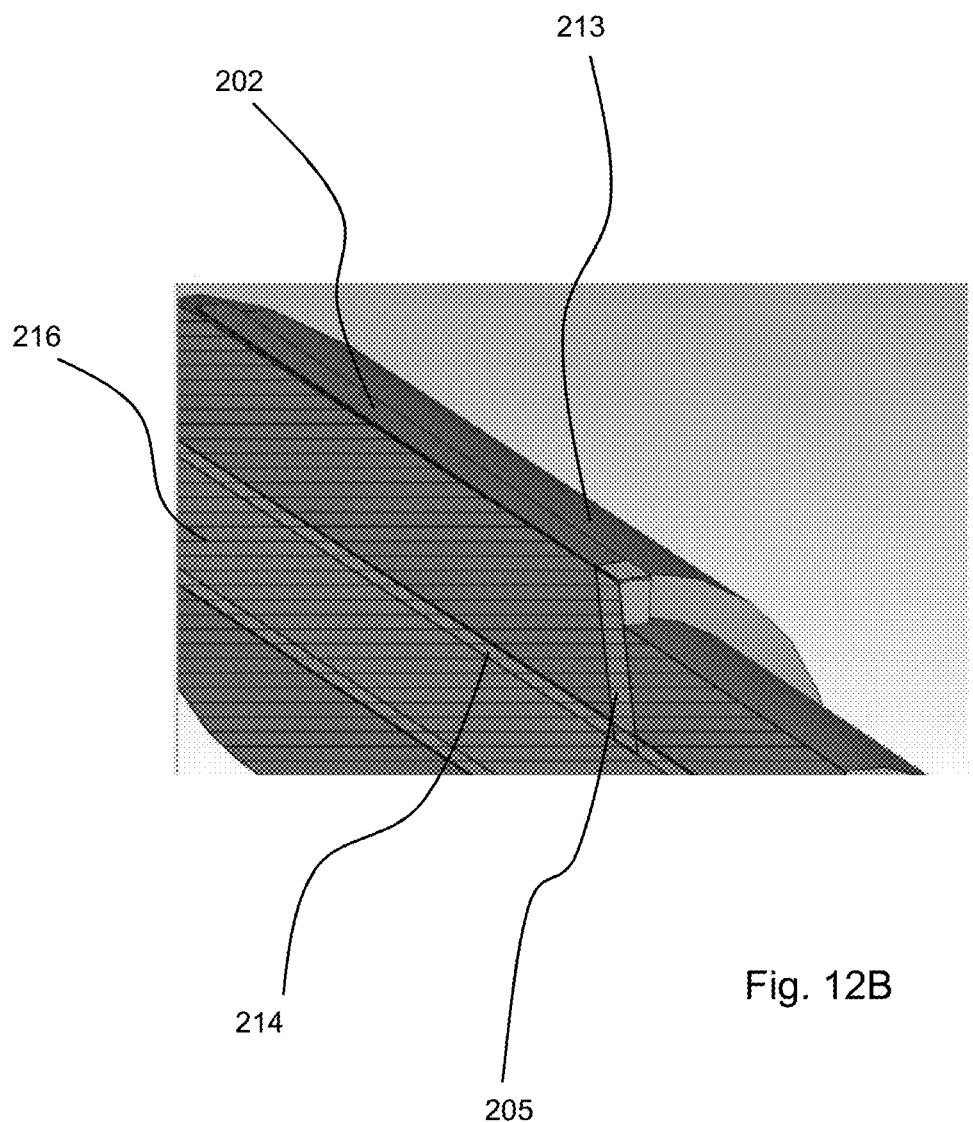

FIG. 12B illustrates in more detail the connection between the outer conductor 214 of the coaxial transmission line 216 and the proximal end of the second (or third) conducting strip 202. A conductive projection 205 extends radially from the outer conductor 214, terminating at the outer cylindrical surface 213 of the second dielectric material. The exposed end surface of the conductive projection 205 then provides an electrical connection point for electrically connecting the outer conductor 214 with the second conducting strip 202 which is located on the outer cylindrical surface 213. A similar arrangement is located circumferentially opposite the conductive projection 205 shown in FIG. 12B, for connection with the other conducting strip which forms part of the second electrode.

Figure 12C:
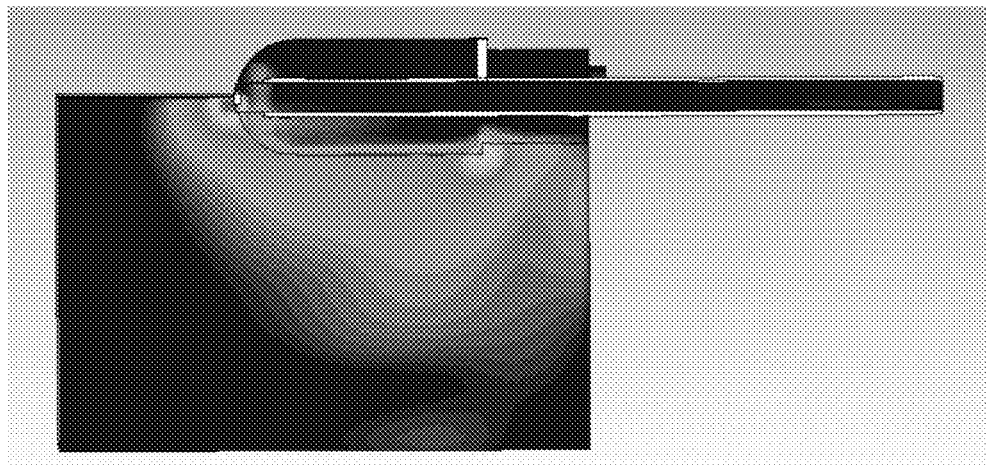
Figure 12D:
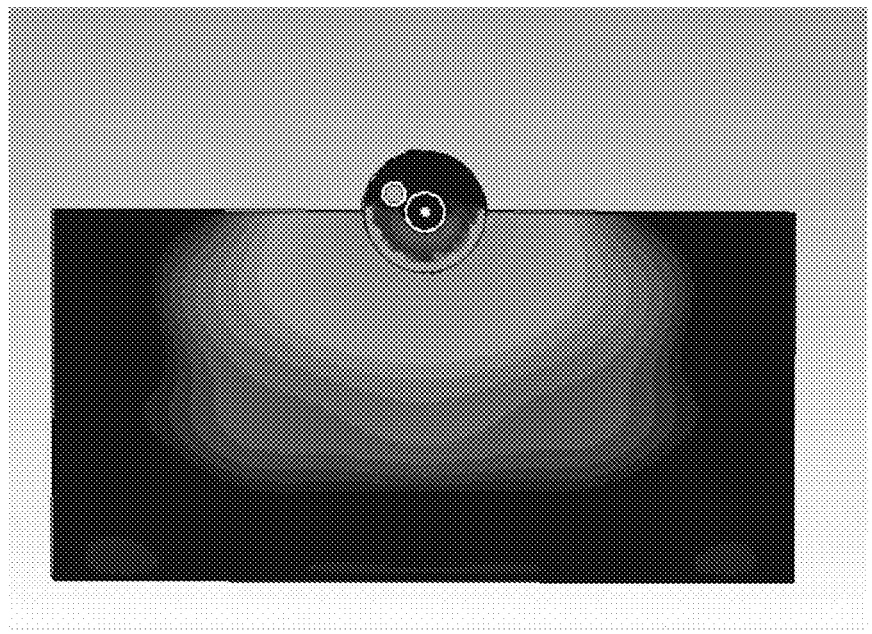

FIGS. 12C and 12D show power absorption plots when the probe tip structure shown in FIGS. 12A and 12B are placed side-on into a liver load.

Figure 13:
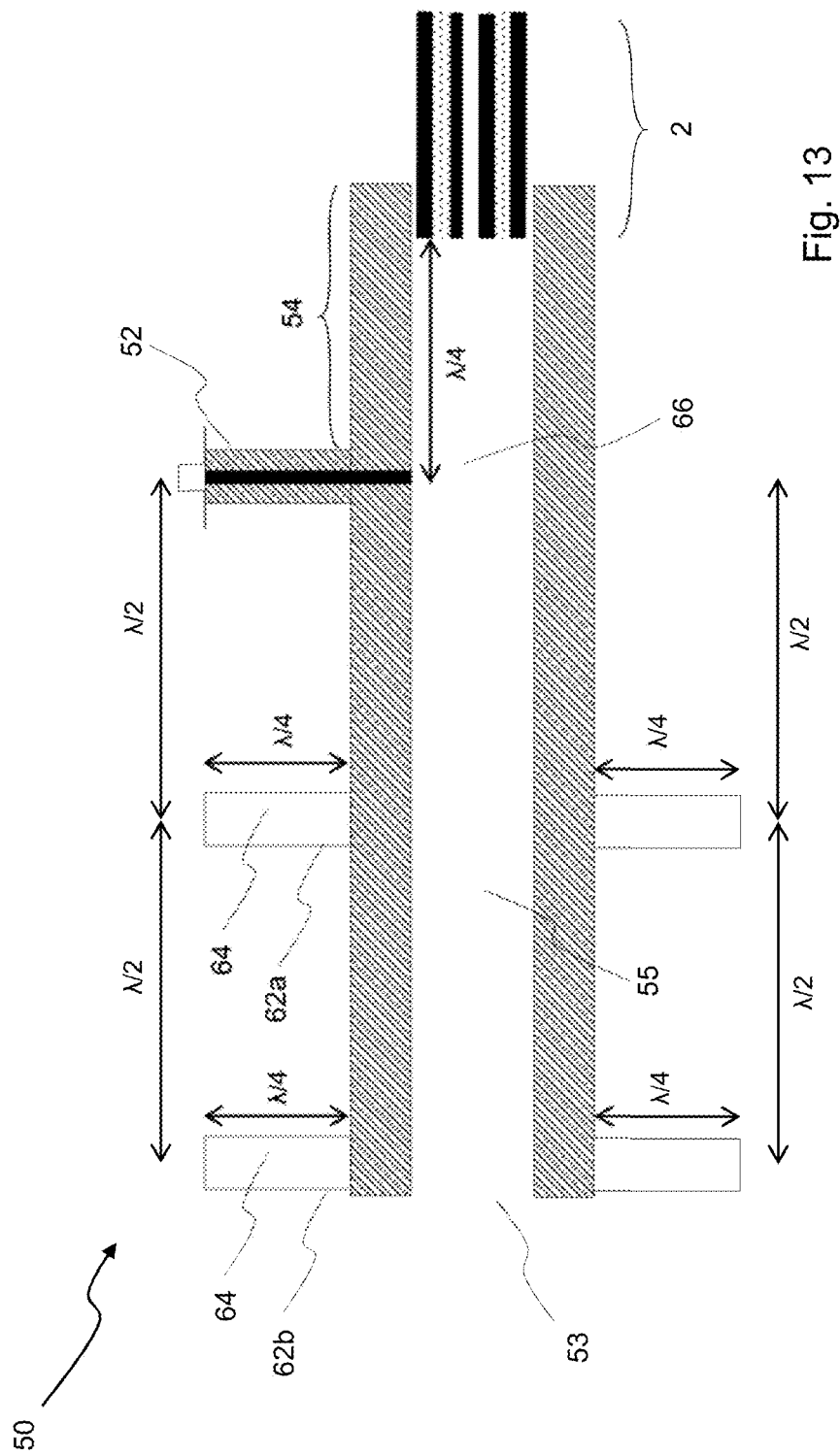
FIG. 13 is a schematic view of an impedance transformer structure which may be used in embodiments of an electrosurgical apparatus incorporating the electrosurgical instrument of the present invention.

FIG. 13 shows an assembly 50 designed to allow RF and microwave EM energy to be introduced to a geometry that includes one or more channels for surgical instruments, gas or fluid to be conveyed to a treatment site. The assembly 50 comprises a signal generator input feed 52 for connection with a signal generator (not shown), an impedance transformer section 54 and two chokes 62a, 62b to ensure good matching and optimum power delivery through the coaxial transmission line 2, which forms part of the electrosurgical instrument of the present invention. At the far left, port 53 may be connected to a liquid source and/or gas source (not shown) to introduce liquid and/or gas into passageway 55, from where it can pass into the electrosurgical instrument of the present invention, e.g. through one or more passageway in or adjacent the coaxial transmission line 2. In this example, the coaxial transmission line includes a hollow inner conductor for conveying liquid.

The impedance transforming section 54 may have a geometry selected so that its impedance matches the impedance of the signal generator with the impedance of the coaxial transmission line 2. This impedance is calculated using the following formula, where $Z_{match}$ is the impedance of the impedance transforming section 54, $Z_{coax}$ is the impedance of the coaxial transmission line 2, and $Z_{SG}$ is the impedance of the signal generator:

$$Z_{match} = \sqrt{Z_{coax} Z_{SG}}$$

The assembly 50 includes two chokes 62a, 62b. The chokes 62a, 62b consist of an air-filled ring 64 oriented perpendicular to the longitudinal axis of the assembly 50, and having a radius that is a quarter-wavelength of the microwaves which are to be supplied to the instrument, which is approximately 12.9 mm at 5.8 GHz. This structure prevent microwaves at the input feed 52 from "splitting" at the T-junction, to ensure that they are only conveyed to the coaxial transmission line 2. The air gap 64 forces an open circuit at that point. The presence of two chokes 62a, 62b, which are spaced a half-wavelength (approximately 25.8 mm at 5.8 GHz) apart, and a half-wavelength from the junction 66, ensures that the entire structure to the left of the junction 66 as shown in FIG. 13 appears as an open circuit irrespective of what may be connected to the port 53 at the far right. Hence, no microwaves pass through the hollow channel 55.

The signal generator input feed 52 is connected perpendicular to the longitudinal axis (in this case, the +z direction) of the assembly 50, a quarter-wavelength away from the junction 66 with the coaxial transmission line 2, to provide a quarter wave matching section between the impedance of the signal generator input feed 52 and the coaxial transmission line 2.

Figure 14A:
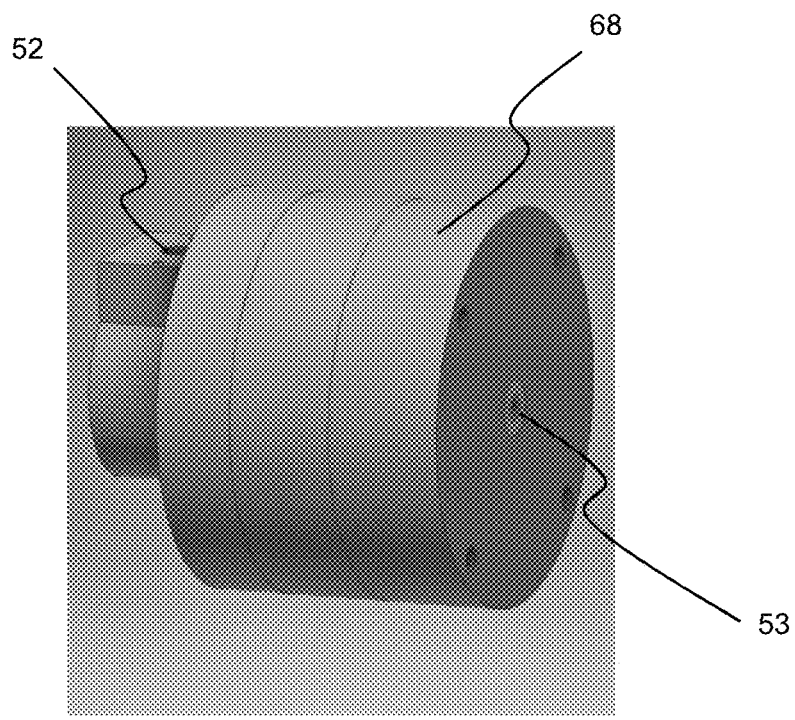
FIGS. 14A and 14B are perspective drawings of the impedance transformer shown schematically in FIG. 13.
Figure 14B:
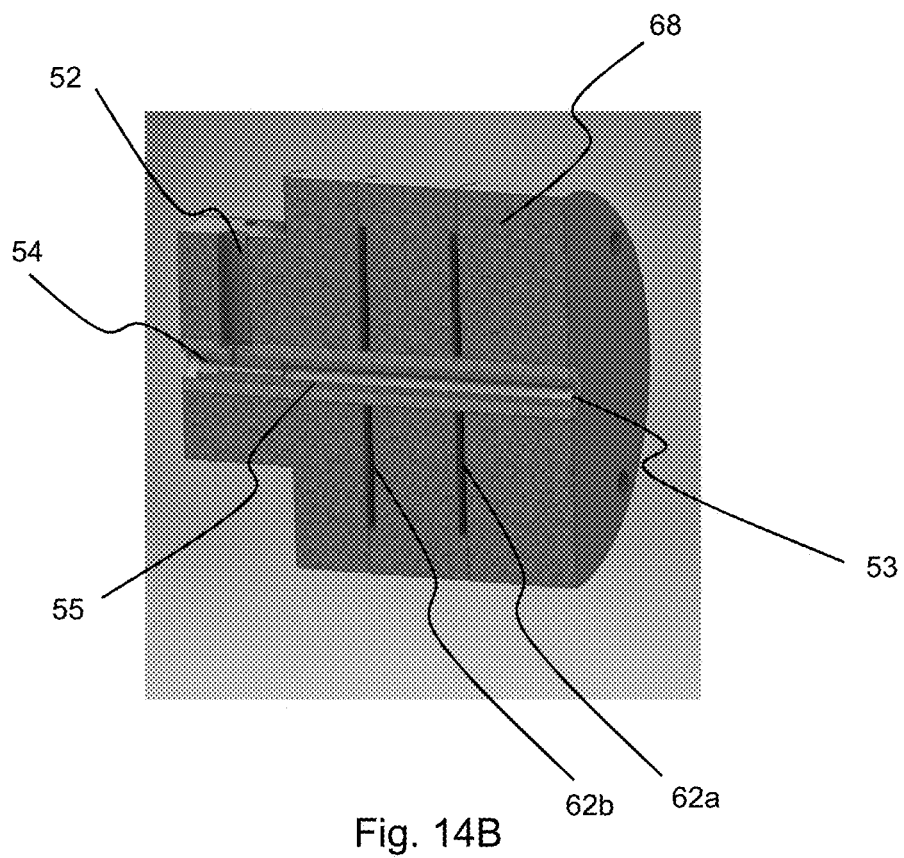
Figure 15:
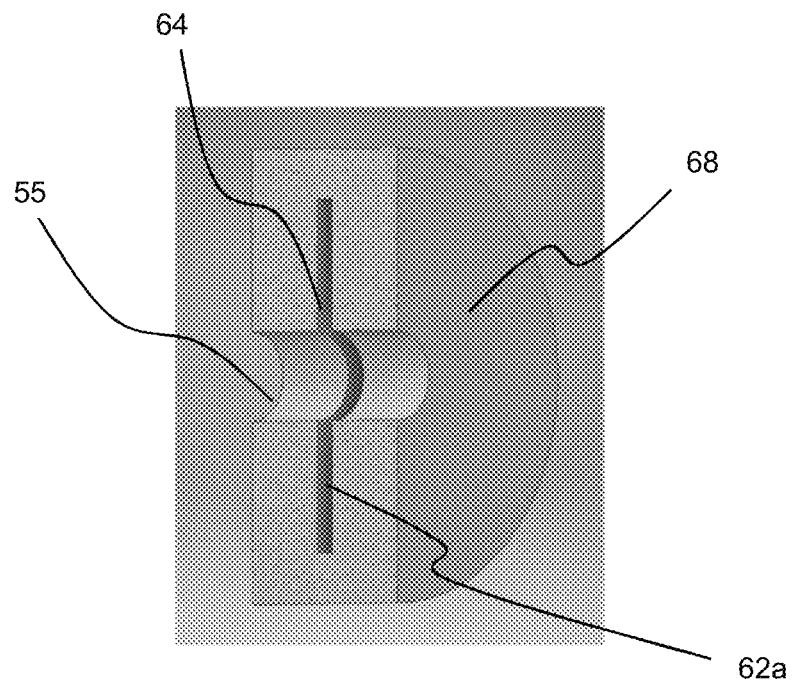
FIG. 15 is a perspective drawing showing a cut away of the choke structures shown in FIGS. 13 and 14A.

FIGS. 14A and 14B show a perspective view of the impedance transformer structure. Housing 68 in the embodiment shown is made of brass. The outside shape of the housing 68 has no electromagnetic effect at 5.8 GHz, as long as the brass is at least one micron thick. Other suitable materials for the housing include aluminium, gold, silver and copper. FIG. 15 shows a perspective cut-away of one of the chokes 62a in the housing 68.

Figure 16:
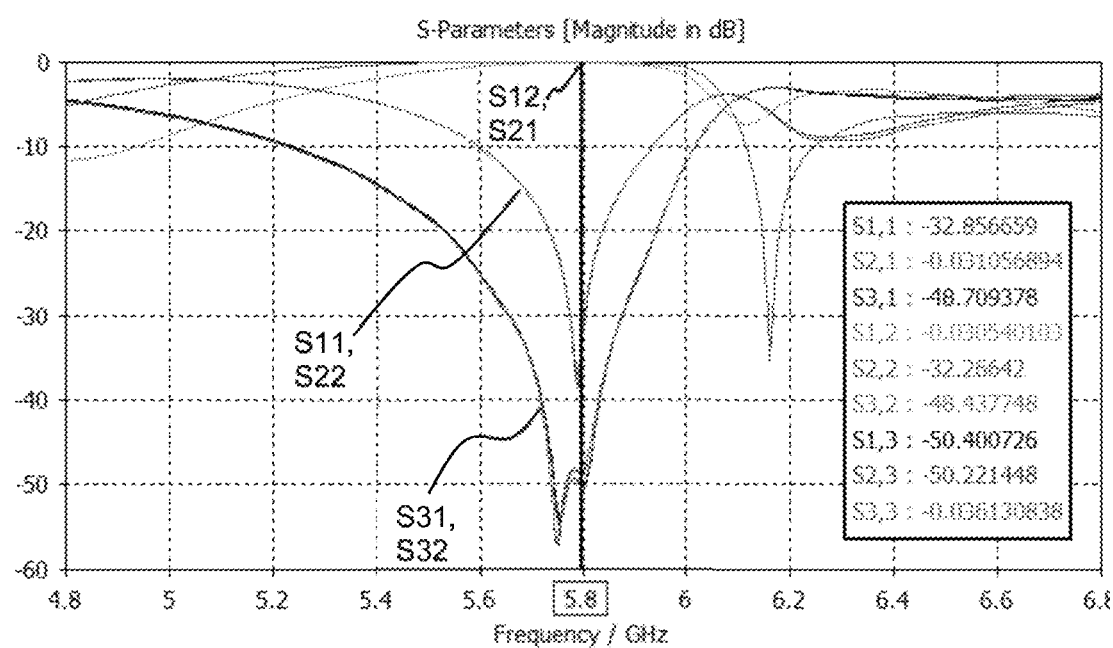
FIG. 16 is a graph showing the reflections/transmissions at interfaces of the impedance transformer structure shown in FIGS. 13 to 15.

FIG. 16 is a graph showing the reflection at each port and the transmission between each pair of ports. Port 1 is the connection to the signal generator input feed 52, port 2 is the connection to the coaxial transmission line 2, and port 3 is the end of the isolated hollow channel 55 at the right. Lines S21, S12 give the transmission from the coaxial transmission line 2 to the signal generator input feed and vice versa, and show 99.3% (−0.03 dB) transmission at 5.8 GHz. Line S11 represents the power reflected at the signal generator input feed 52, and line S22 represents the power reflected by the coaxial transmission line 2, which are both 0.07% (−32 dB). Shown by lines S32 and S31, the leakage power from the end of the isolated hollow channel 55 are less than 0.0016% (−48 dB) from the coaxial transmission line 2 or the signal generator input feed 52 respectively.

Thus, the impedance transformer structure as shown demonstrates excellent performance at the frequencies in question.

The invention claimed is:

1. An electrosurgical instrument having an elongate probe comprising:
    a coaxial transmission line for conveying radiofrequency (RF) or microwave electromagnetic (EM) radiation;
    a probe tip at a distal end of the coaxial transmission line for receiving the RF or microwave energy;
    a liquid channel for conveying liquid to the probe tip; and
    a gas channel for conveying gas to the probe tip;
    wherein the coaxial transmission line includes an inner conductor, an outer conductor, and a first dielectric material separating the inner conductor from the outer conductor,
    wherein the probe tip comprises a rigid second dielectric material having a probe tip channel running therethrough, the probe tip channel being in fluid communication with the liquid channel and terminating in an aperture at its distal end,
    wherein the probe tip includes a first electrode connected to the inner conductor of the coaxial transmission line and a second electrode connected to the outer conductor of the coaxial transmission line, the first electrode and the second electrode each comprising a conductive structure on an outer surface of the probe tip and being selectively operable in a plasma generating mode or a non-ionising radiation mode,
    wherein, in the plasma generating mode, the first electrode and second electrode are arranged around a flow path of gas from the gas channel over the outer surface of the probe tip, whereby the RF or microwave EM energy from the coaxial transmission line is deliverable to strike and sustain a thermal or non-thermal plasma in gas delivered along the flow path, and
    wherein, in the non-ionising radiation mode, at least one of the first electrode and the second electrode is configured as a radiating antenna structure for emitting a microwave EM field outwardly from the probe tip.

2. An electrosurgical instrument according to claim 1, wherein the gas channel and liquid channel comprise separate pathways that are not in fluid communication with each other.

3. An electrosurgical instrument according to claim 1, wherein one or both of the liquid channel and the gas channel are located inside the coaxial transmission line.

4. An electrosurgical instrument according to claim 3, wherein the gas channel comprises a longitudinal passageway through the first dielectric material, and the liquid channel comprises a longitudinal passageway running through the inner conductor.

5. An electrosurgical instrument according to claim 1, wherein the first dielectric material comprises a multi-layered dielectric structure having a first layer configured to protect against breakdown when conveying the RF energy, and a second layer configured to support low loss propagation of the microwave EM energy.

6. An electrosurgical instrument according to claim 5, wherein the first layer can withstand a peak RF voltage of 800 V, and the second layer has a loss tangent equal to or less than 0.0001.

7. An electrosurgical instrument according to claim 1, wherein the probe tip has a proximal end connected to the distal end of the coaxial transmission line, and a distal end opposite to the proximal end that is shaped in a smoothly contoured manner to be suitable for applying a pressure spot to a target area.

8. An electrosurgical instrument according to claim 1, wherein the radiating antenna structure comprises a monopolar structure formed by the first electrode.

9. An electrosurgical instrument according to claim 1, wherein the radiating antenna structure comprises a conductive structure that has cylindrical symmetry.

10. An electrosurgical instrument according to claim 1, wherein the first electrode comprises a portion of the inner conductor that extends through the probe tip.

11. An electrosurgical instrument according to claim 10, wherein the conductive structure of the first electrode is electrically connected to a distal end of the portion of the inner conductor that extends through the probe tip.

12. An electrosurgical instrument according to claim 10, wherein the conductive structure of the second electrode is electrically connected to the outer conductor and electrically isolated from the inner conductor.

13. An electrosurgical instrument according to claim 12, wherein the second electrode comprises a conducting ring on the outer surface of the probe tip, the conducting ring being electrically connected to the outer conductor.

14. An electrosurgical instrument according to claim 12, wherein the first electrode comprises a first conducting strip on the outer surface of the probe tip, and the second electrode comprises a second conducting strip on the outer surface of the probe tip.

15. An electrosurgical instrument according to claim 12, wherein the first electrode comprises a first conducting strip located on the outer surface of the probe tip, the first conducting strip including a first limb and a second limb that are disposed on opposite sides of the probe tip, the first limb and the second limb meeting at the distal end of the probe tip, and wherein the second electrode comprises a second conducting strip which is located on the outer surface of the probe tip at a position between the first limb and the second limb of the first conducting strip.

16. An electrosurgical instrument according to claim 15, wherein the second electrode further includes a third conducting strip which is located on an opposite side of the outer surface of the probe tip to the second conducting strip.

17. An electrosurgical instrument according to claim 16 wherein the outer conductor of the coaxial transmission line includes first and second conductive projections at its distal end for electrically connecting, respectively, to the proximal ends of the second and third conducting strips.

18. An electrosurgical instrument according to claim 1, wherein the first electrode and the second electrode comprise a helical electrically conductive structure.

19. An electrosurgical instrument according to claim 18, wherein:
the first electrode is an inner helical electrode,
the second electrode is a first outer helical electrode,
the inner helical electrode has a smaller diameter than the first outer helical electrode,
the inner helical electrode follows the same path as the first outer helical electrode, and
the first outer helical electrode and the inner helical electrode form a transmission line structure for conveying RF and microwave EM energy from the proximal end of the probe tip to the distal end of the probe tip.

20. An electrosurgical instrument according to claim 19, wherein the first outer helical electrode is on an outer surface of the probe tip, and the inner helical electrode is located directly beneath the first outer helical electrode, and is at least partially embedded in the probe tip.

21. An electrosurgical instrument according to claim 20, further including a second outer helical electrode on the outer surface of the probe tip, diametrically opposite the first outer helical electrode, and having the same pitch,
wherein the second outer helical electrode is electrically connected to the inner helical electrode at a distal end, such that microwave/RF energy received at the distal end of the probe tip from the transmission line structure results in corresponding microwave/RF signals being excited between the first outer helical electrode and the second outer helical electrode, to generate an electric field there between.

22. An electrosurgical instrument according to claim 18, wherein the helical electrically conductive structure comprises a first helical electrode and a second helical electrode formed in an axially offset relationship on the outer surface of the probe tip, the first helical electrode and second helical electrode being electrically isolated from each other to form a coplanar transmission line.

23. An electrosurgical instrument according to claim 1, wherein the probe tip channel contains a hollow needle, having a first end in fluid communication with the liquid channel and a second end opposite to the first end, for dispensing liquid to a target area.

24. An electrosurgical instrument according to claim 23, wherein the needle is adjustable between:
a retracted position, in which the second end of the needle is located inside the probe tip channel or liquid channel, and
an exposed position, in which the second end of the needle is located outside the probe tip channel, past the aperture at its distal end.

25. An electrosurgical instrument according to claim 24 comprising means for preventing supply of microwave energy or RF energy to the probe tip when the needle is in the exposed position.

26. An electrosurgical instrument according to claim 25, wherein the means includes a switch mechanism configured to break an electrical connection to the probe tip when the needle is in the exposed position.

27. An electrosurgical instrument according to claim 26, wherein the inner conductor of the coaxial transmission line has an axial gap, and wherein the needle is coupled to move with an electrically conductive bridge element that is movable between a connecting position where it provides an electrical connection over the axial gap when the needle is in the retracted position and an isolating position where it exposes the axial gap when the needle is in the exposed position.

28. An electrosurgical apparatus for performing coagulation having:
   a microwave signal generator for generating microwave EM energy;
   a radiofrequency (RF) signal generator for generating RF EM energy having a frequency lower than the microwave EM frequency;
   an electrosurgical instrument according to claim 1 connected to receive the RF EM energy and the microwave EM energy;
   a feed structure for conveying the RF EM energy and the microwave EM energy to the probe, the feed structure including
      a microwave channel for connecting the coaxial transmission line to the microwave signal generator,
      an RF channel for connecting the coaxial transmission line to the RF signal generator,
      a gas feed connected to supply gas to the electrosurgical instrument, and
      a liquid feed connected to supply liquid to the electrosurgical instrument,
   wherein the apparatus is selectively operable:
      in a plasma-generating mode for surface coagulation, whereby the microwave EM energy and RF energy delivered to the probe tip are arranged to strike and sustain a gas plasma between the first and second electrodes;
      in a non-ionising radiation mode, whereby the microwave EM energy delivered to the probe tip is arranged to emit a non-ionising EM field outwardly from the probe tip for tissue coagulation; and
      in a liquid administration mode, whereby liquid is supplied to a target area via the liquid feed, the liquid channel and the aperture at the distal end of the probe tip channel.

29. An electrosurgical apparatus according to claim 28 that is further selectively operable in a RF coagulation mode, where RF energy is applied between the first electrode and second electrode to coagulate tissue.

30. An electrosurgical apparatus according to claim 28 or 29, wherein, in the non-ionising radiation mode, the RF EM energy is supplied with the microwave energy in order to augment the coagulation effect.

31. An electrosurgical apparatus according to claim 28 comprising a strike signal generation unit arranged to cause a pulse of RF EM energy to be delivered to the probe tip to generate an electric field between the first electrode and the second electrode, in order to strike a plasma therebetween.

32. An electrosurgical apparatus according to claim 28 comprising an assembly for matching impedance between the feed structure and the coaxial transmission line of the electrosurgical instrument, the assembly comprising:
   a signal generator input feed for receiving signals from the RF/microwave signal generator;
   a transformer output arranged to deliver signals to the coaxial transmission line of the electrosurgical instrument; and
   an impedance matching section located between the signal generator input feed and the transformer output, and having dimensions and an impedance selected to match the impedance between the signal generator input feed and the coaxial transmission line,
   wherein the assembly includes a hollow channel, having a liquid/gas input port at one end, and which meets the impedance matching section at the other end, the hollow channel arranged to deliver liquid and gas to the liquid channel and gas channel of the electrosurgical instrument via the impedance matching section.

33. An electrosurgical apparatus according to claim 32, wherein the assembly comprises a choke structure located on the hollow channel on the opposite side of the signal generator input feed to the impedance matching section.

34. An electrosurgical apparatus according to claim 33, wherein a distance separating the choke structure and a junction between the hollow channel and the signal generator input feed is equal to half a wavelength of the microwave energy received at the signal generator input feed.

* * * * *

UNITED STATES PATENT AND TRADEMARK OFFICE
CERTIFICATE OF CORRECTION

| | |
|---|---|
| PATENT NO. | : 10,820,937 B2 |
| APPLICATION NO. | : 15/781442 |
| DATED | : November 3, 2020 |
| INVENTOR(S) | : Christopher Paul Hancock |

It is certified that error appears in the above-identified patent and that said Letters Patent is hereby corrected as shown below:

On the Title Page

Item [71], delete:
"Beaufort Park Way (GB)"
And insert:
-- Chepstow (GB) --

Signed and Sealed this
Twelfth Day of January, 2021

Andrei Iancu
*Director of the United States Patent and Trademark Office*